(12) United States Patent
DiCarlo et al.

(10) Patent No.: US 7,901,770 B2
(45) Date of Patent: Mar. 8, 2011

(54) EMBOLIC COMPOSITIONS

(75) Inventors: Paul DiCarlo, Middleboro, MA (US); Robert F. Rioux, Ashland, MA (US); James Tobin, Lincoln, MA (US); Barbara Bell, Sudbury, MA (US); Thomas V. Casey, II, Grafton, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 180 days.

(21) Appl. No.: 10/791,103

(22) Filed: Mar. 2, 2004

(65) Prior Publication Data

US 2005/0095428 A1     May 5, 2005

Related U.S. Application Data

(63) Continuation of application No. 10/700,403, filed on Nov. 4, 2003, now abandoned.

(51) Int. Cl.
*B32B 5/66* (2006.01)
(52) U.S. Cl. ......... 428/402; 428/403; 428/404; 428/405; 428/406; 428/407; 623/23.73
(58) Field of Classification Search .......... 428/402–407; 606/108; 604/83.01; 623/1.18
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Moiser |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |

(Continued)

FOREIGN PATENT DOCUMENTS

AU          A-76186/98          10/1998

(Continued)

OTHER PUBLICATIONS

Abbara, S. et al., "Transcervical Expulsion of a Fibroid as a Result of Uterine Artery Embolization for Leiomyomata", *JVIR*, vol. 10, No. 4, pp. 409-411; 1999.

(Continued)

*Primary Examiner* — Leszek Kiliman
(74) *Attorney, Agent, or Firm* — Fish & Richardson P.C.

(57) ABSTRACT

Embolic compositions and methods of delivering the compositions are disclosed. In some embodiments, the embolic compositions include a shape memory material.

20 Claims, 12 Drawing Sheets

U.S. PATENT DOCUMENTS

| | | | |
|---|---|---|---|
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A * | 3/1993 | Kamiya et al. ............... 606/213 |
| 5,263,992 A | 11/1993 | Guire |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,443,495 A | 8/1995 | Buscemi et al. |
| 5,468,801 A | 11/1995 | Antonelli et al. |
| 5,469,854 A | 11/1995 | Unger et al. |
| 5,514,379 A | 5/1996 | Weissleder et al. |
| 5,583,162 A | 12/1996 | Li et al. |
| 5,585,112 A | 12/1996 | Unger et al. |
| 5,595,821 A | 1/1997 | Hager et al. |
| 5,733,925 A | 3/1998 | Kunz et al. |
| 5,741,331 A | 4/1998 | Pinchuk |
| 5,756,127 A | 5/1998 | Grisoni et al. |
| 5,770,222 A | 6/1998 | Unger et al. |
| 5,779,668 A | 7/1998 | Grabenkort |
| 5,840,387 A | 11/1998 | Berlowitz-Tarrant et al. |
| 5,888,930 A | 3/1999 | Smith et al. |
| 5,895,398 A | 4/1999 | Wensel et al. |
| 5,902,832 A | 5/1999 | Van Bladel et al. |
| 5,902,834 A | 5/1999 | Porrvik |
| 5,922,025 A | 7/1999 | Hubbard |
| 6,048,908 A | 4/2000 | Kitagawa |
| 6,056,721 A | 5/2000 | Shulze |
| 6,056,844 A | 5/2000 | Guiles et al. |
| 6,160,084 A | 12/2000 | Langer et al. |
| 6,165,193 A | 12/2000 | Greene, Jr. et al. |
| 6,179,817 B1 | 1/2001 | Zhong |
| 6,191,193 B1 | 2/2001 | Lee et al. |
| 6,214,384 B1 | 4/2001 | Pallado et al. |
| 6,245,090 B1 | 6/2001 | Gilson et al. |
| 6,251,661 B1 | 6/2001 | Urabe et al. |
| 6,280,457 B1 | 8/2001 | Wallace et al. |
| 6,296,604 B1 | 10/2001 | Garibaldi et al. |
| 6,296,622 B1 * | 10/2001 | Kurz et al. ............... 604/93.01 |
| 6,296,632 B1 | 10/2001 | Luscher et al. |
| 6,306,419 B1 | 10/2001 | Vachon et al. |
| 6,306,425 B1 | 10/2001 | Tice et al. |
| 6,312,407 B1 | 11/2001 | Zadno-Azizi et al. |
| 6,312,942 B1 | 11/2001 | Plüss-Wenzinger et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,503,272 B2 * | 1/2003 | Duerig et al. ............... 623/1.24 |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,575,896 B2 | 6/2003 | Silverman et al. |
| 6,602,261 B2 * | 8/2003 | Greene et al. ............... 606/108 |
| 6,605,111 B2 * | 8/2003 | Bose et al. ............... 623/1.18 |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 7,131,997 B2 * | 11/2006 | Bourne et al. ............... 623/23.72 |
| 7,449,236 B2 * | 11/2008 | Lanphere et al. ............... 428/402 |
| 7,588,780 B2 * | 9/2009 | Buiser et al. ............... 424/501 |
| 7,591,993 B2 | 9/2009 | Boschetti |
| 2002/0054912 A1 | 5/2002 | Kim et al. |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0108614 A1 | 6/2003 | Volkonsky et al. |
| 2003/0183962 A1 | 10/2003 | Buiser et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0203985 A1 | 10/2003 | Baldwin et al. |
| 2003/0206864 A1 | 11/2003 | Mangin |
| 2003/0215519 A1 | 11/2003 | Schwarz et al. |
| 2003/0233150 A1 | 12/2003 | Bourne et al. |
| 2004/0076582 A1 | 4/2004 | DiMatteo et al. |
| 2004/0091543 A1 | 5/2004 | Bell et al. |
| 2004/0092883 A1 | 5/2004 | Casey et al. |
| 2004/0096662 A1 | 5/2004 | Lanphere et al. |
| 2004/0101564 A1 | 5/2004 | Rioux et al. |
| 2004/0186377 A1 | 9/2004 | Zhong et al. |
| 2005/0025800 A1 | 2/2005 | Tan |
| 2005/0037047 A1 | 2/2005 | Song |

FOREIGN PATENT DOCUMENTS

| | | |
|---|---|---|
| DE | 3834705 | 4/1990 |
| DE | 297 24 255 U1 | 10/2000 |
| EP | 0 067 459 | 12/1982 |
| EP | 0122624 | 10/1984 |
| EP | 0123235 | 10/1984 |
| EP | 0 243 165 | 10/1987 |
| EP | 0 294 206 | 12/1988 |
| EP | 0 422 258 A1 | 10/1989 |
| EP | 0458745 A1 | 5/1991 |
| EP | 0458079 A2 | 11/1991 |
| EP | 0067459 B2 | 10/1998 |
| EP | 0 764 047 | 8/2003 |
| EP | 0 993 337 | 4/2004 |
| ES | 2 096 521 | 3/1997 |
| JP | 2-277459 | 11/1990 |
| JP | 9-110678 | 4/1997 |
| JP | 9-165328 | 6/1997 |
| JP | 9-316271 | 12/1997 |
| JP | 2000189511 | 7/2000 |
| JP | 2001079011 | 3/2001 |
| JP | 2003-528130 | 9/2003 |
| JP | 2007-510464 | 4/2007 |
| NZ | 255409 | 2/1997 |

| | | |
|---|---|---|
| NZ | 517377 | 8/2003 |
| TW | 421658 | 2/2001 |
| WO | WO91/12823 | 5/1991 |
| WO | WO 93/00063 | 1/1993 |
| WO | WO 95/33553 | 12/1995 |
| WO | WO 96/37165 | 11/1996 |
| WO | WO 98/04616 | 2/1998 |
| WO | WO98/26737 | 6/1998 |
| WO | WO 99/00187 | 1/1999 |
| WO | WO 99/42528 | 8/1999 |
| WO | 99/46327 | 9/1999 |
| WO | WO 99/51278 | 10/1999 |
| WO | WO 00/32112 | 6/2000 |
| WO | 00/66183 | 11/2000 |
| WO | WO 01/12359 | 2/2001 |
| WO | WO 01/66016 | 9/2001 |
| WO | WO 01/72281 | 10/2001 |
| WO | WO01/93920 | 12/2001 |
| WO | WO 02/34300 | 5/2002 |
| WO | WO 03/013552 | 2/2003 |
| WO | WO 03/016364 | 2/2003 |
| WO | WO03/051451 | 6/2003 |
| WO | WO03/084582 | 10/2003 |
| WO | WO 2004/019999 | 3/2004 |
| WO | WO2004/020011 | 3/2004 |
| WO | WO 2004/040972 | 5/2004 |
| WO | WO2004/073688 | 9/2004 |
| WO | WO 2004/075989 | 9/2004 |
| WO | WO2005/044145 | 5/2005 |

OTHER PUBLICATIONS

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling http://www.altcorp.com/AffinityLabeling/ablaeling.htm, pp. 1-6, May 20, 2003.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with [88]Y: Conjugation, Labeling, Biodistribution studies", 2 pages, 2000 http://www.kernchemie.uni-mainz.de/downloads/jb2000/b14_brockmann.pdf.

Carroll, B.A. et al., "Microbubbles as Ultrasonic Contrast Agents", *Investigative Radiology*, vol. 14, No. 3, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1; Feb. 1980.

Carstensen, E.L. et al., "Determination of the Acoustic Properties of Blood and its Components", *Journal of Acoustical Society of America*, vol. 25, No. 2; Mar. 1953.

Cirkel, U. et al., "Experience with Leuprorelin Acetate Depot in the Treatment of Fibroids: A German Multicentre Study", *Clinical Therapeutics*, vol. 14, Suppl. A, 1992.

Deasy, P. B., "*Microencapsulation and Related Drug Processes*", New York, NY, Marcel Dekker, Inc., 345 pages, 1984 (Table of Contents only).

DeGast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Goldberg, B.B., "Ultrasonic Cholangiography", *Radiology*, vol. 118, pp. 401-404, Feb. 1976.

Gramiak, R. et al., "Ultrasound Cardiography: Contrast Studies in Anatomy and Function", *Radiology*, vol. 92, No. 5, pp. 939-948, Apr. 1969.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001 www.iop.org/Journals/pb.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kerber, C., "Balloon Catheter with a Calibrated Leak", *Radiology*, vol. 120, pp. 547-550, Sep. 1976.

Kochan, J.P. et al., "Interventional Neuroradiology: Current Practices and Techniques at Temple University Hospital" http://www.temple.edu/radiology/stroke.html, 5 pages.

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp.

Lendlein, A. et al., "Biodegradable, Elastic Shape-Memory Polymers for Potential Biomedical Applications", *Science*, vol. 296, pp. 1673-1676, May 31, 2002.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods http://www.ims.uconn.edu/-mather, 4 pages.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003 http://www.tandf.co.uk/journals.

Sirtex Medical Limited—Product Description http://www.sirtex.com/?p=72 (Retrieved from the Internet on May 27, 2003).

Sirtex Medical Limited—Targeted Radiotherapy with SIR-Spheres http://www.sirtex.com/?p=57 (Retrieved from the Internet on May 27, 2003).

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

"Improving a Key Weapon Against Cancer", Research Horizons, Spring/Summer 2001, pp. 11-12.

"Contour® PVA Particles," Boston Scientific, http://www.bostonscientific.com, 2 pages (Retrieved from the Internet on Sep. 6, 2005).

Hori et al., "Management of peripheral AVMs by embolotherapy using SAP-microsphere," *European Congress of Radiology*, Abstract 1024, http://www.ecr.org/conferences/ecr1997/sciprg/abs/9701024o.htm, 1 page (Retrieved from the Internet on Dec. 2, 2003).

Minamitani et al., "Embolization therapy of neoplastic lesions using a new embolic material without antineoplastic agents," *European Congress of Radiology*, Abstract 1499, http://www.ecr.org/conferences/ecr1997/sciprg/abs/9701499o.htm, 1 page (Retrieved from the Internet on Dec. 2, 2003).

FeRx Incorporated, FERX Profile http://www.biotechshares.com/FERX.htm, 4 pages, Retrieved from the Internet on Jun. 26, 2003.

Laurent, A., "Materials and Biomaterials for Interventional Radiology", *Biomed & Pharmacother* 1998:52: 76-88.

International Search Report and Written Opinion for PCT/US2004/036195, mailed Jul. 14, 2005.

"Pulmonary artery pseudoaneurysm/aneurysm" Available Web Site: http://www.mamc.amedd.army.mil/williams/chest/vascular/paaneurysm/paaneyrysm.htm.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583 Available Web Site: http://www.hepatitis-central.com/hcv/hcc/embolization/references.html.

Buhle, Jr. el, "Re: Re: Hepatic Arterial Embolization", *UCLA Medicine Online* Available Web Site: http://www.meds.com/archive/mol-cancer/1996/msg00128.html.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244-1255.

Gohel, et al., "Formulation design and optimization of modified-release microspheres of diclofenac sodium", *Drug Dev Ind Pharm*, vol. 25, No. 2, pp. 247-251, 1999, abs: http://www.ncbi.nlm.nih.gov/entrez/query.fcgi?cmd=retrieve&db=PubMed&list_uids=10065360&dop=A..., pp. 1, 2002.

Kim, et al., "Composite poly(vinyl alcohol) beads for controlled drug delivery", *Pharm Res*, vol. 9. No. 1, pp. 10-16, 1992, abs: http://www.ncbi.nlm.nih.gov/entrez/query.fcgi?cmd=retrieve&db=PubMed&list_uids=1589392&dopt=Abs..., pp. 1, 2002.

Kurata, et al., "Preoperative embolization for meningiomas using PVA particles", *No Shinkei Geka*, vol. 20, No. 4, pp. 367-373, 1992, abs: http://www.ncbi.nlm.nih.gov/entrez/query.fcgi?cmd=retrieve&db=PubMed&list_uids=1570057&dopt=Abs..., pp. 1, 2002.

Nakstad, et al., "Embolization of intracranial arteriovenous malformations and fistulas with polyvinyl alcohol particles nad platinum fibre coils", *Neuroradiology*, vol. 34, No. 4, pp. 348-351, 1992, abs: http://www.ncbi.nlm.nih.gov/entrez/query.fcgi?cmd=retrieve&db=PubMed&list_uids=15284..., pp. 1, 2002.

Nash, et al., "Modifications of polystyrenic matrices for the purification of proteins. II. Effect of the degree of glutaraldehyde-poly(vinyl alcohol) crosslinking on various dye ligand chromatography systems",*J Chromatogr A*, vol. 776, No. 1, pp. 55-63, 1997, abs: http://www.ncbi.nlm.nih.gov/entrez/query.fcgi?cmd=retrieve&db=PubMed&list_uids=92860..., pp. 1, 2002.

Schwarz, K.Q., "The Acoustic Filter: An Ultrasonic Blood Filter for the Heart-Lung Machine," *J Thoracic and Cardiovascular Surgery* 104(6):1647-1653 (1992).

Shafik, A., "Intraesophageal Polytef injection for the treatment of reflux esophagitis", *Department of Surgery and Experimental Research, Faculty of Medicine, Cairo University*, Cairo, Egypt, pp. 1-2, Received: Jun. 22, 1994; Accepted: Oct. 15, 1994 http://www.ahmedshafik.org/Group-D/d016.htm.

Thanoo, et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Thanoo, et al., "Tantalum loaded silicone micropsheres as particulate emboli", *J Microencapsul*, vol. 8, No. 1, pp. 95-101, 1991, abs:http://www.ncbi.nlm.nih.gov/entrez/query.fcgi?cmd=retrieve&db=PubMed&list_uids=1880697&dop=Abs..., pp. 1, 2002.

Worthington-Kirsch RL, 1999, "Interventionalists offer management option for uterine fibroids." Diagnostic Imaging, pp. 47-49. Available Web Site: http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Zou, Ying-hua et al., "Experimental Canine Hapatic Artery Embolization with Polyvinyl Alcohol Microspheres", (Translation) *Zong Hua Fang-She Xue ZaZhi*, Dec. 23, 1989 (6): 330-332.

Bourke et al., "Protein Drug Release from Photocrosslinked Poly(vinyl alcohol) Hydrogels," *Society for Biomaterials 28th Annual Meeting Transactions*, p. 144 (2002).

Capozza et al., "Endoscopic treatment of vesico-ureteric reflux and urinary incontinence: technical problems in the paediatric patient," *British Journal of Urology*, 75(4):538-542 (Apr. 1995).

Cruise et al., "In Vitro and In Vivo Characterization of a Hydrogel-Based Aneurysm Embolization System," *Society for Biomaterials 28th Annual Meeting Transactions*, p. 203 (2002).

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Gramiak et al., "Echocardiography of the Aortic Root," *Investigative Radiology*, 3(5):356-366 (Sep.-Oct. 1968).

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Krinick et al., "A polymeric drug delivery system for the simultaneous delivery of drugs activatable by enzymes and/or light," *J. Biomater. Sci. Polymer Edn*, 5(4):303-324 (1994).

Lemperle et al., "PMMA Microspheres for Intradermal Implantation: Part I. Animal Research," *Annals of Plastic Surgery*, 26(1):56-63 (Jan. 1991).

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Maruhashi, "Modified Polyvinyl Alcohols I and II," *Polyvinyl Alcohol—Developments*, John Wiley & Sons, Chichester, England, pp. 160-161 and pp. 186-191 (1992).

Namiki, "Application of Teflon Paste for Urinary Incontinence—Report of 2 Cases," *Uro. Int.*, 39:280-282 (1984).

Orienti et al., "Crosslinked Polyvinylalcohol Hydrogels as Vehicles for Hydrophilic Drugs," *Arch. Pharm. Pharm. Med. Chem.*, 333:421-424 (2000).

Pedley et al., "Hydrogels in Biomedical Applications," *British Polymer Journal*, 12:99-110 (Sep. 1980).

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Progelhof et al., "Table 4.21. Properties of electrical insulating films (101)," *Polymer Engineering Principles: Properties, Processes, and Tests for Design*, Hanser Publishers, Munich, p. 383 (1993).

PVA Plus, AngioDynamics® Inc., "Reliable PVA Foam Formulated for Consistency and Controlled Delivery—Embolization Particles Ordering Information," www.angiodynamics.com (Aug. 2002).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Schetky, "Shape-Memory Alloys," *Encyclopedia of Chemical Technology*, Third Edition, vol. 20, John Wiley & Sons, New York, pp. 726-736 (1982).

Shafik, "Intraesophageal Polytef injection for the treatment of reflux esophagitis," *Surg. Endosc.*, 10:329-331 (1996).

Siskin et al., "Pathologic Evaluation of a Spherical Polyvinyl Alcohol Embolic Agent in a Porcine Renal Model," *J. Vasc. Interv. Radiol.*, 14:89-98 (2003).

Smith et al., "Evaluation of Polydimethylsiloxane as an alternative in the Endoscopic Treatment of Vesicoureteral Reflux," *The Journal of Urology*, 152:1221-1224 (Oct. 1994).

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Strasnick et al., "Transcutaneous Teflon® Injection for Unilateral Vocal Cord Paralysis: An Update," *The Laryngoscope*, 101:785-787 (Jul. 1991).

Tian et al., "Design and synthesis of amphiphilic poly (ethylene glycol) derivatives as micellar drug delivery systems," *Polymer Preprints*, 43(2):719-720 (Fall 2002).

"Fibroid Treatment Collective—Fibroid Embolization" (2 pages), http://www.fibroids.org.

White, Jr., "Embolotherapy in Vascular Disease," *American Journal of Roentgenology*, 142:27-30 (Jan. 1984).

Winters et al., "Periurethral injection of collagen in the treatment of intrinsic sphincteric deficiency in the female patient," *The Urologic Clinics of North America*, 22(3):673-678 (Aug. 1995).

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Zisch et al., "Covalently conjugated VEGF-fibrin matrices for endothelialization," *Journal of Controlled Release*, 72:101-113 (2001).

Kim et al., "Hollow Silica Spheres of Controlled Size and Porosity by Sol-Gel Processing," *J. Am. Ceram. Soc.*, 74(8):1987-1992 (Aug. 1991).

* cited by examiner

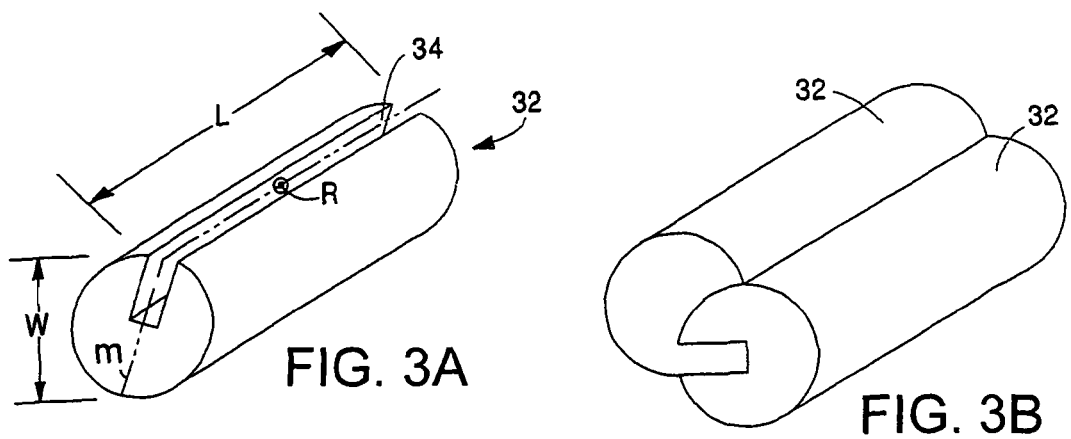
FIG. 3A
FIG. 3B
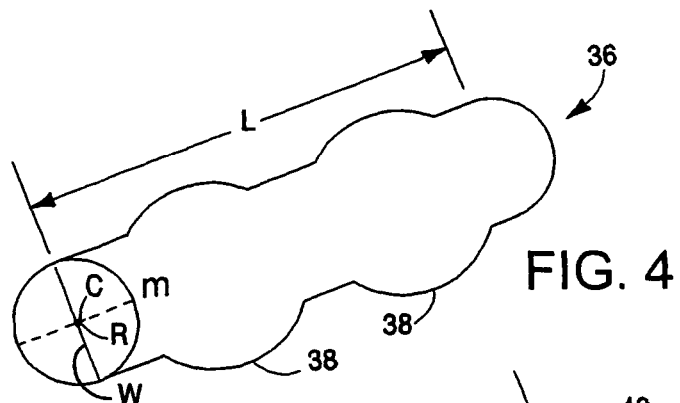
FIG. 4
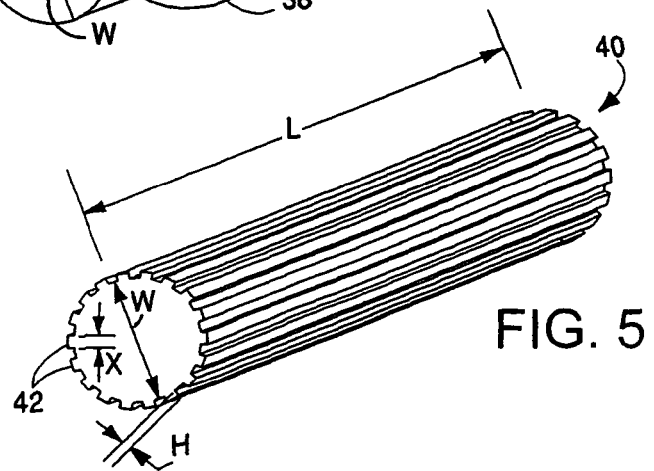
FIG. 5

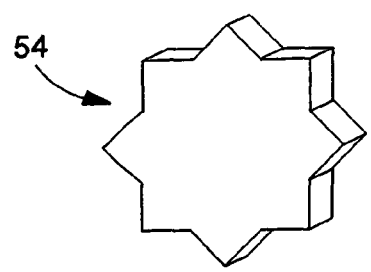
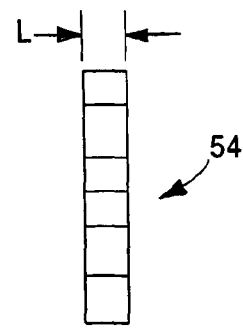
FIG. 11A  FIG. 11B
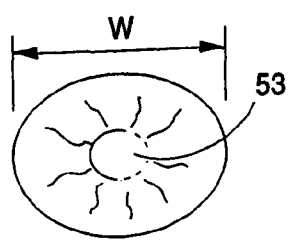
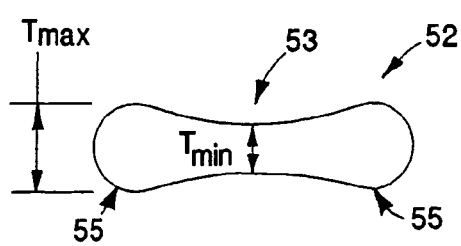
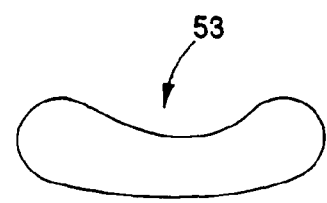
FIG. 10A  FIG. 10B  FIG. 10C

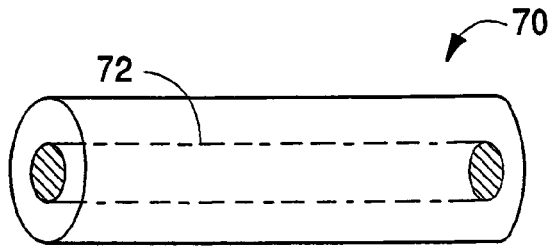
FIG. 16
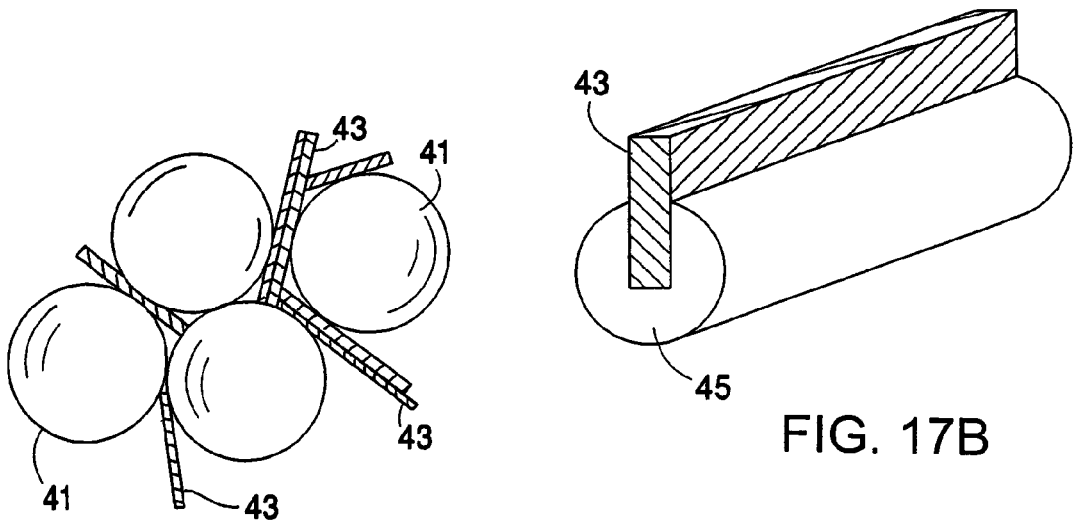
FIG. 17B
FIG. 17A
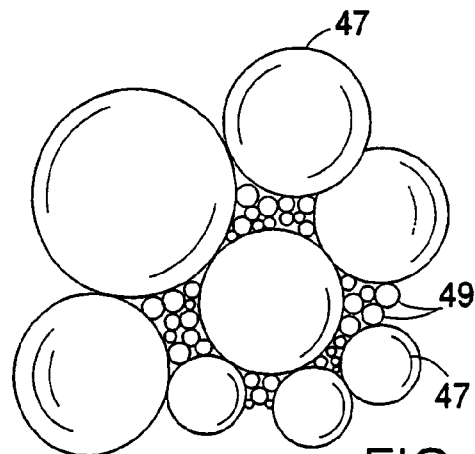
FIG. 18
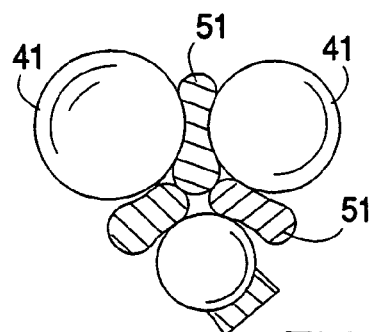
FIG. 19

EMBOLIC COMPOSITIONS

This application is a continuation (and claims the benefit of priority under 35 U.S.C. §120) of U.S. application Ser. No. 10/700,403, filed Nov. 4, 2003 now abandoned.

RELATED APPLICATIONS

This application is related to U.S. application Ser. No. 10/700,970 entitled "Embolic Compositions", and filed on the same day as this application, hereby incorporated by reference.

TECHNICAL FIELD

The invention relates to embolic compositions and methods of using the compositions.

BACKGROUND

Embolic compositions can be used to prevent or to treat certain conditions in the body. For example, in therapeutic vascular occlusions (sometimes called "embolizations"), particulate embolic compositions can be used to block, or occlude, vessels in the body. The embolic compositions can be used to block microvascular supplies of blood to tumors (thereby depriving the tumors of resources to grow), or to block hemorrhagic conditions in the body (thereby reducing or stopping bleeding). The compositions can be delivered to a target site using a catheter that has been introduced into the vessel.

SUMMARY

In one aspect, the invention features a composition comprising an embolic particle including a shape memory material.

Embodiments may include one or more of the following features. The shape memory material includes a polymer and/or an alloy. The particle is non-resorbable in a body. The particle includes a therapeutic agent, for example, the particle can define a cavity, and the therapeutic agent can be in the cavity. The particle includes a radiopaque material. The particle has a portion capable of dissolving in a body. The particle further has a second material that does not include a shape memory material.

Embodiments of compositions may include one or more of the following features. The composition includes a plurality of embolic particles, wherein at least one of the particles includes the shape memory material. The composition further includes a second plurality of embolic particles, a particle in the second plurality having a different shape than a particle in the plurality of embolic particles. For example, the composition includes a spherical particle and a non-spherical particle. The composition further includes a second plurality of embolic particles, a particle in the second plurality having a different size than a particle in the plurality of embolic particles. The composition further includes a second plurality of embolic particles, a particle in the second plurality having a different hardness than a particle in the plurality of embolic particles. The composition further includes a second, non-solid embolic material, such as one in the form of a liquid, a gel, or a foam. The particle includes a material, such as a hydrogel, capable of increasing in volume upon exposure to a predetermined stimulus.

Embodiments may include one or more of the following shapes. The particle is non-spherical, e.g., oblate. The particle is elongated and has a length to width ratio greater than one. The particle is generally cylindrical. The particle includes a groove extending along a longitudinal direction. The particle has a first cross section having a first width, and a second cross section parallel to the first cross section and having a second width different than the first width. The particle has a groove. The particle has a ridge on its outer surface extending along a longitudinal direction. The particles have a plurality of ridges on its outer surface extending along a longitudinal direction. The particle has a cross section having a plurality of symmetrical vertices. The particle has a triangular cross section.

In another aspect, the invention features a kit including a composition having an embolic particle including a shape memory material, and a catheter sized for delivering the composition into a body. The kit can include a contrast agent. The composition can include a plurality of particles.

In another aspect, the invention features a composition including a non-spherical embolic particle having an element of symmetry.

Embodiments may include one or more of the following features. The element of symmetry is an axis of symmetry and/or a plane of symmetry. The particle has the form of a cylinder, and the axis of symmetry extends longitudinally along the cylinder. The particle has a groove. The cylinder has at least two radial cross sections having different diameters. The cylinder has a plurality of ridges on is outer surface extending along a longitudinal direction. The particle has a cross section including a plurality of symmetrical vertices. The particle has a length to width ratio greater than one. The particle has a triangular cross section. The particle includes a shape memory material. The particle includes a therapeutic agent and/or a radiopaque material.

In another aspect, the invention features a method including introducing an embolic composition into a body, the composition having a particle in a first configuration, changing the particle from the first configuration to a second configuration in the body, and occluding a site in the body with the particle in the second configuration.

The method can further include exposing the particles to a change in energy, e.g., temperature. The method can further include delivering a second embolic composition into the body.

Other aspects and features of the invention will be apparent from the description of the preferred embodiments and from the claims.

DESCRIPTION OF DRAWINGS

FIG. 3A is an illustration of an embodiment of an embolic particle having a slot; and FIG. 3B is an illustration of two of particles of FIG. 3A interlocking.

FIG. 4 is an illustration of an embodiment of an embolic particle having enlarged portions.

FIG. 5 is an illustration of an embodiment of an embolic particle having ridges.

FIG. 10A is a top view of an embodiment of an oblate embolic particle; FIG. 10B is a side view of the particle of FIG. 10A; and FIG. 10C shows the particle of FIG. 10A in a flexed position.

FIGS. 11A and 11B are illustrations of an embodiment of a star-shaped embolic particle.

FIG. 16 is an illustration of an embodiment of an embolic particle having a cavity.

FIG. 17A is an illustration of an embodiment of an occlusion; and FIG. 17B is an illustration of two embolic particles interlocking.

FIG. 18 is an illustration of an embodiment of an occlusion.

FIG. 19 is an illustration of an embodiment of an occlusion.

DETAILED DESCRIPTION

Figure 1A:
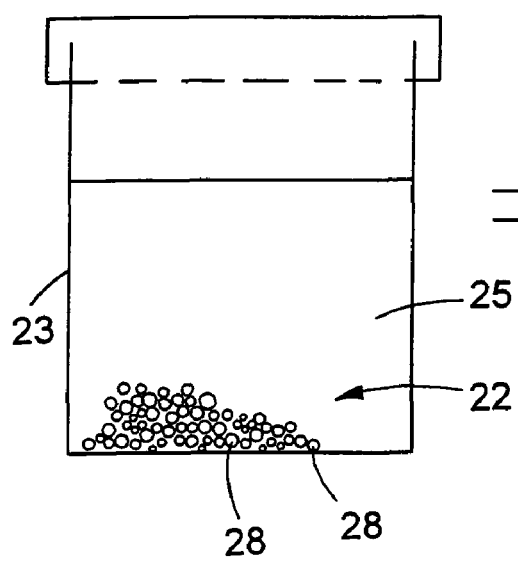
FIGS. 1A and 1B illustrate an embodiment of an embolic composition in a first state and in a second state, respectively.
Figure 1B:
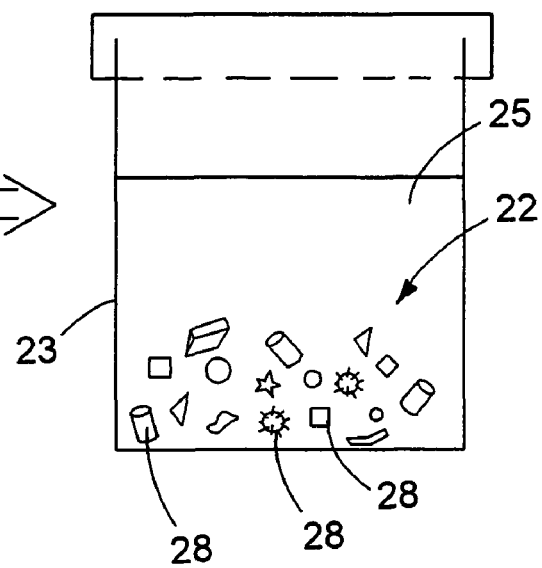

Referring to FIGS. 1A and 1B, an embolic composition 22 includes a collection of particles 28. Particles 28 may be contained in a vessel 23 with a suitable carrier 25, such as saline, prior to use. Referring particularly to FIG. 1A, particles 28 are in a first state in which the particles have a common shape, such as a compacted, generally spherical shape. Referring to FIG. 1B, particles 28 are illustrated in a second state in which the particles have a less compacted shape. The transition between the states, and the shape change of the particles, can be selectively triggered to facilitate treatment, e.g., embolization.

Figure 2A:
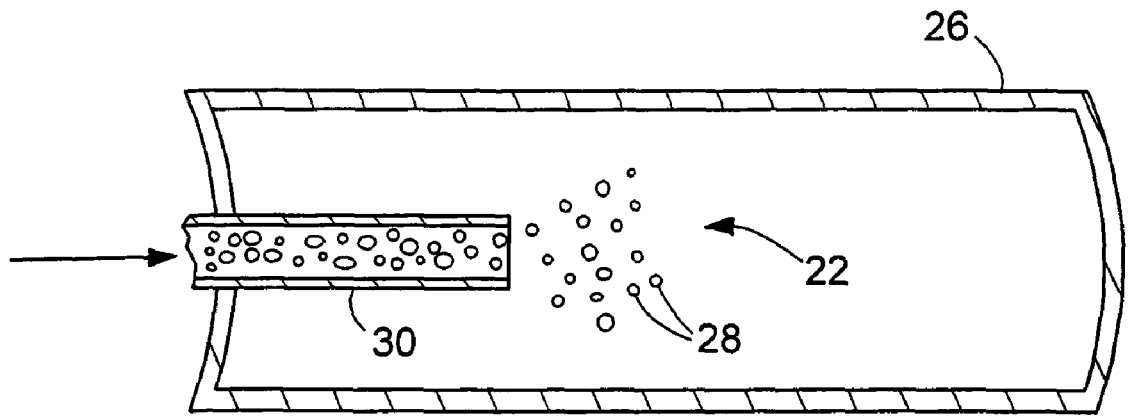
FIGS. 2A, 2B, and 2C illustrate an embodiment of a method of delivering an embolic composition.
Figure 2B:
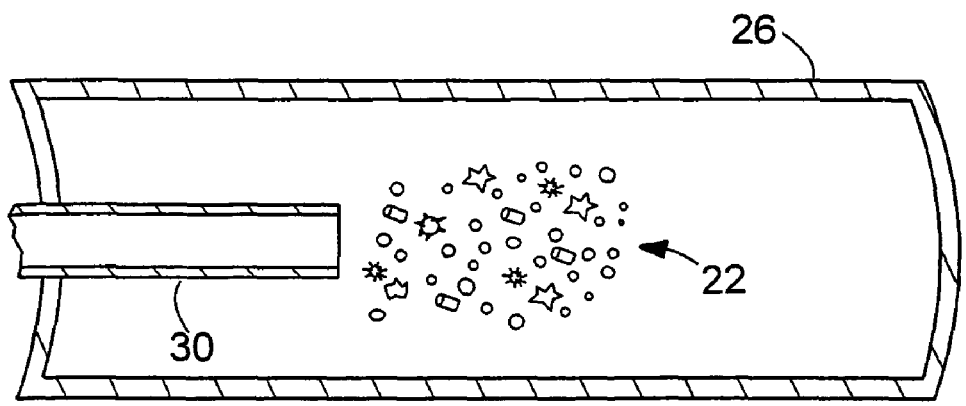
Figure 2C:
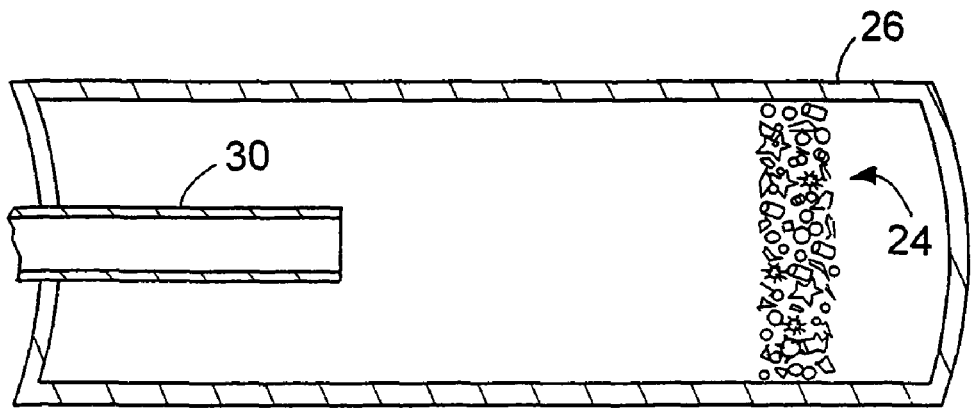

Composition 22 can be delivered to a target site 24 in a vessel 26 using a catheter 30. Referring to FIGS. 2A-2C, during delivery through catheter 30, particles 28 are in the first state and have a compacted shape that provides flowability to avoid clogging or aggregation in catheter 30. After particles 28 are released from catheter 30, the particles are transitioned to the second state to form a second shape, such as an enlarged, non-compacted shape. Particles 28, in their second shape, then flow within vessel 26, aggregate, and block the vessel, thereby depriving a tumor or reducing hemorrhaging, for example.

Particles 28 can include a shape memory material, which is capable of being configured to remember, e.g., to change to, a predetermined configuration or shape. The shape memory material is capable of transitioning between states and shapes based on exposure to environmental conditions, such as temperature, pH, or energy input, e.g., electromagnetic radiation. The shape memory material can provide a permanent occlusion, i.e., the occlusion is not substantially absorbed by the body and/or is not intended to be removed from the body. Particles 28 can be formed at least in part or wholly of a shape memory material.

The shape memory material can be, for example, a polymer or an alloy. Suitable shape memory polymers include elastomers that exhibit melt or glass transitions at temperatures that are above body temperature, e.g., at about 40 to 50° C., and safe for use in the body. Examples of polymers include shape memory polyurethanes (available from Mitsubishi), polynorbornene (e.g., Norsorex™ (Mitsubishi)), polymethylmethacrylate (PMMA), poly(vinyl chloride), polyethylene (e.g., crystalline polyethylene), polyisoprene (e.g., transpolyisoprene), styrene-butadiene copolymer, rubbers, or photocrosslinkable polymer including azo-dye, zwitterionic and other photochromic materials (as described in Shape Memory Materials, Otsuka and Wayman, Cambridge University Press, 1998). Other shape memory polymers include shape memory plastics available from MnemoScience GmbH Pauwelsstrasse 19, D-52074 Aachen, Germany. Mixtures of polymeric shape memory materials can be used.

In some embodiments, the shape memory polymer is crosslinked and/or crystalline. The degree of crosslinking and/or crystallinity is sufficient to resist excessive creep or stress relaxation, e.g., after the polymer is heated. Crosslinking can also be controlled to adjust the melt or glass transition temperature and transition temperature range. In some cases, a narrow transition range, e.g. 10° C., 5° C., or less, is desirable. Crosslinking can be achieved by application of radiation, such as e-beam, UV, gamma, x-ray radiation, or by heat-activated chemical crosslinking techniques (e.g., with peroxides). In some radiation crosslinking techniques, the polymer need not be substantially heated to achieve crosslinking.

In some embodiments, the shape memory polymer is formed or set to a primary (e.g., stress free) shape during crosslinking. For example, an embolic particle can be crosslinked in a final shape. Subsequently, the polymer can be formed into a temporary shape, for example, by heating the polymer to a softening point (e.g., $T_m$ or $T_g$), deforming (e.g., compacting) the polymer, and cooling the polymer to below a softening point. When the polymer is subsequently heated to above the softening temperature, the polymer can recover to its primary form.

The shape memory material can be an alloy, such as a superelastic or pseudo-elastic metal alloy. An example of a superelastic materials include Nitinol™ (e.g., 55% nickel, 45% titanium), which can be heated and formed from a first shape to a second shape. When the Nitinol™ material is cooled, the material stays in the second shape. Subsequently, if the material is heated to a predetermined transition temperature, the material can transition to the first shape. Other examples of superelastic materials include silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium ($Fe_3Be$), iron platinum ($Fe_3Pt$), indium-thallium (In—Tl), iron-manganese (Fe—Mn), nickel-titanium-vanadium (Ni—Ti—V), iron-nickel-titanium-Cobalt (Fe—Ni—Ti—Co) and copper-tin (Cu—Sn). See, e.g., Schetsky, L. McDonald, "Shape Memory Alloys", Encyclopedia of Chemical Technology (3rd ed.), John Wiley & Sons, 1982, vol. 20. pp. 726-736 for a full discussion of superelastic alloys. The shape memory alloy can be coated with a polymer, which may or may not have shape memory properties.

A variety of techniques can be used to form shape memory material into embolic particles. Examples of suitable techniques include microelectromechanical (MEM) techniques, micromachining, nanomachining, nanoetching, and/or nanoassembly. The particles can be formed by extrusion (e.g., of elongated particles), molding, and/or by stamping a sheet of shape memory material (e.g., having a thickness equal to the length of the particles).

Mixtures of shape memory materials can be used to make a particle. For example, a particle can include a relatively hard core (e.g., made of Nitinol™) and a relatively soft outer surface (e.g., made of a polymer). The soft outer surfaces allow the particles to deform slightly, thereby enhancing packing when the particles aggregate.

The particles can be sterilized by a low temperature technique such as electron-beam irradiation, and packaged, e.g., about 1 to 5 ml of particles in about 5 to 10 ml saline. In embodiments, electron beam irradiation can be used to pharmaceutically sterilize the particles to reduce bioburden. In e-beam sterilization, an electron beam is accelerated using magnetic and electric fields, and focused into a beam of energy. This resultant beam can be scanned by means of an electromagnet to produce a "curtain" of accelerated electrons. The accelerated electron beam penetrates the collection of embolic particles to confer upon them electrons that destroy bacteria and mold to sterilize and reduce the bioburden in the embolic particles. Electron beam sterilization can be carried out by sterilization vendors such as Titan Scan, Lima, Ohio.

As described above, the particles can be selectively transitioned from a first state to the second state. The transition of the shape memory material from its temporary configuration to its final configuration can be effected, for example, using a catheter carrying a heating device, such as a resistive heater or radiofrequency (RF) heater provided in the interior of the catheter. Alternatively or in addition, the shape memory material can be compounded to include a material, such as magnetic particles, that is susceptible to heating by magnetic effects, such as hysteresis effects. A magnetic field can be imposed on the particles by a source on a catheter or outside the body. Suitable magnetic particles are available as the Smartbond™ System from Triton Systems, Inc., Chelmsford, Mass. Heating by magnetic effects is discussed in U.S. Pat. No. 6,056,844, hereby incorporated by reference. Other methods for effecting the transition of the shape memory material include introducing an interactive or reactive (i.e., non-inert) material, such as a fluid through the catheter, and into the body after the particles are released from the catheter. For example, the fluid can be heated to the transition temperature (e.g., about 30-60° C.) and/or have a predetermined pH to effect the transition. In other embodiments, a change in energy (e.g., temperature) can be produced by passing an optic fiber through the catheter to deliver optical energy, such ultraviolet or infrared radiation.

After the particles are transformed into their second shape, the particles can flow within the vessel, aggregate, and block the vessel. As described below, particles 28 can be formed in a variety of shapes that enhance aggregation, and numerous embodiments of compositions 22 and methods of delivering the compositions are possible.

In some embodiments, embolic particle 28 has an elongated shape, as exemplified by the embodiments shown in FIGS. 3A and 4-7. That is, particle 28 has a length, L, that is greater than a width or diameter, W. The length, L, is the longest dimension of particle 28, and can range from about 100 microns to about 1200 microns. For example, the length, L, can be greater than or equal to about 100, 200, 300, 400, 500, 600, 700, 800, 900, 1000, or 1100 microns; and/or less than or equal to about 1200, 1100, 1000, 900, 800, 700, 600, 500, 400, 300, or 200 microns. The width or diameter, W, is the average dimension taken along a plane transverse (e.g., orthogonal) to the direction of length, L. The width or diameter, W, can range from about 50 microns to about 1000 microns. For example, W can be greater than or equal to about 50, 100, 200, 300, 400, 500, 600, 700, 800, or 900 microns; and/or less than about 1000, 900, 800, 700, 600, 500, 400, 300, 200, or 100 microns. In some cases, the largest dimension of the particle is equal to or less than the smallest dimension of the instrument (e.g., microcatheter) used to deliver the particles.

Expressed another way, embolic particle 28 can have a length (L) to width/diameter (W) aspect ratio of greater than one. (A spherical particle would have a length to width aspect ratio of one.) In some embodiments, particle 28 has a length to width aspect ratio of from about 1.25:1 to about 10:1. For example, the aspect ratio can be greater than or equal to about 1.25:1, 2:1, 3:1, 4:1, 5:1, 6:1, 7:1, 8:1, or 9:1; and/or less than or equal to about 10:1, 9:1, 8:1, 7:1, 6:1, 5:1, 4:1, 3:1, or 2:1.

As shown in FIGS. 3A and 4-7, an elongated particle 28 can have different shapes. For example, FIGS. 3A, 4 and 5 show different embodiments of elongated particles having a generally tubular shape. FIG. 3A shows an embolic particle 32 in the shape of a cylinder having a slot or a groove 34 extending along the length of the particle. Slot 34 allows particle 32 to be more easily compacted, e.g., for delivery, and facilitates interaction between the particles, e.g., by allowing the slots to engage (e.g., interlock) with each other and the particles to self-assemble (FIG. 3B). Slot 34 can extend the entire length of particle 32, or only a portion thereof. Particle 32 can include multiple slots 34, for example, the slots can be arranged collinearly along the particle, and/or distributed (symmetrically or asymmetrically) around the circumference of the particle. In some embodiments, particle 32 does not include slot 34, i.e., the particle can be a conventional cylinder.

FIG. 4 shows an embolic particle 36 in the shape of a cylinder having enlarged portions 38. In use, enlarged portions 38 help particles 36 to engage or mate with each other, thereby enhancing aggregation, e.g., by providing a more closely-packed mass. Portions 38 are generally curvilinear or rounded portions having a diameter greater than the diameter of other portions of particle 36. In some embodiments, enlarged portions 38 have a maximum diameter of about 1,500 microns (e.g., less than about 1,200, 1,000, 800, 600, or 400 microns). Particle 36 can include one or more enlarged portions 38.

FIG. 5 shows an embolic particle 40 in the shape of cylinder having a plurality of ridges 42 extending along the length of the particle. As with slot 34 and enlarged portions 38, ridges 42 can help particles 40 engage or lock with each other during use. Ridges 42 can extend the entire length of particle 40, or only a portion thereof. Ridges 42 can be symmetrically or asymmetrically formed about the circumference of particle 40. In some embodiments, ridges 42 have a maximum height, H, of about 100 microns (e.g., less than about 100, 80, 60, or 40 microns), and a base width, X, of about 50 microns. Ridges 42 can have different cross-sectional shapes, such as square, rectangular, or triangular.

Figure 6:
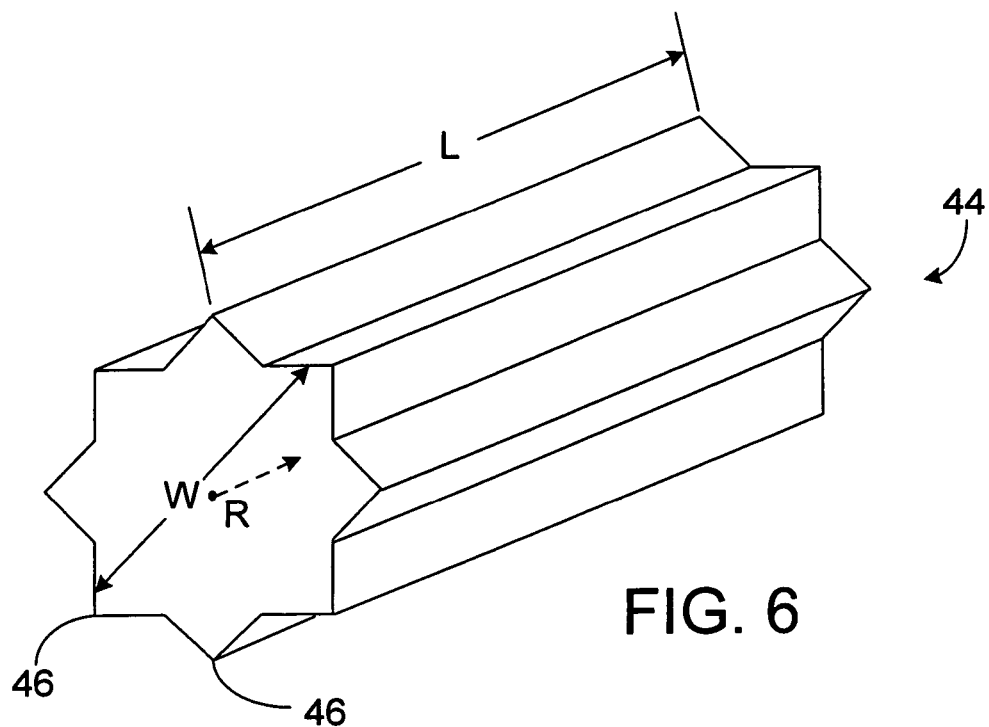
FIG. 6 is an illustration of an embodiment of an embolic particle having a cross section with vertices.
Figure 7:
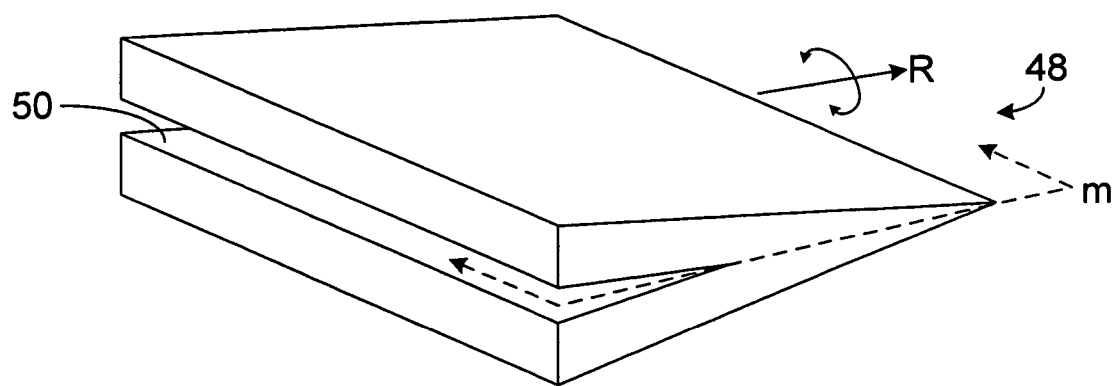
FIG. 7 is an illustration of an embodiment of an embolic particle having a slot.

Indeed, as shown in FIGS. 3A and 4-7, the embolic particles can have a variety of cross-sectional shapes. For example, FIGS. 3A and 4 show particles 32 and 36 having generally circular cross sections. FIG. 5 shows particle 40 having a generally gear-shaped cross section. FIG. 6 shows a star-shaped embolic particle 44 having a cross section with multiple (as shown, eight) vertices 46. In some embodiments, particle 44 can have one, two, three, four, five, six, seven, or more vertices 46, arranged symmetrically or asymmetrically around the particle. As another example, FIG. 7 shows an embolic particle 48 having a triangular cross section and a slot 50. Particle 48 further illustrates that the embolic particles can have uniform or non-uniform Particle 48, along with particles 40 and 44, also illustrate that the outer surface of the particles can be faceted, vis-à-vis cylindrical or rod-like (e.g., FIG. 3A). In other embodiments, the embolic particles can have other cross sectional shapes, for example, other non-circular shapes, such as oval, elliptical, or regularly or irregularly polygonal having 3, 4, 5, 6, 7, or 8 or more sides.

The embolic particles shown in FIGS. 3A and 4-7 also exemplify a class of embolic particles that can be characterized as having an element of symmetry. In comparison, a mass having a random shape typically does not include an element of symmetry. An example of an element of symmetry is a mirror plane, in which the structure of the particle is identical at corresponding, mirror-imaged locations on both sides of the plane. For example, particles 32 and 48 have a mirror plane (m) extending through the middle of slots 34 and 50, respectively (FIGS. 3A and 7). Particle 36 has an infinite number of mirror planes extending along the length of the particle and intersecting the cross-sectional center, C (FIG. 4). Particle 44 has numerous mirror planes, for example, extending along the length of the particle and intersecting the middle of a vertex 46, respectively (FIG. 6). Another example of an element of symmetry is an axis of symmetry about which rotation at selected (but not 360°) intervals yields the identical orientation. For example, particle 36 has an axis of symmetry, R, extending through the cross-sectional center about which rotation in any increment would yield the identical orientation (FIG. 4). Particle 44 also has an axis of symmetry, R, extending through the cross-sectional center about which rotation in 45° increments would yield the identical orientation (FIG. 6). Particles 32 and 48 have an axis of symmetry, R, about which rotation in 180 degrees increments would yield the identical orientation.

In addition, while the particles described above include certain discrete features (such as a slot, an enlarged portion, or a ridge), in some embodiments, an embolic particle can include multiple features, in any combination. For example, particle 36 with enlarged portions 38 can further include one or more slots and/or one or more ridges. Star-shaped particle 44 can include one or more slots and/or one or more enlarged portions. Wedged-shaped particle 48 may not include a slot, but can include, for example, one or more ridges. Any combination of features can be used to enhance interaction among the particles during use.

Figure 8A:
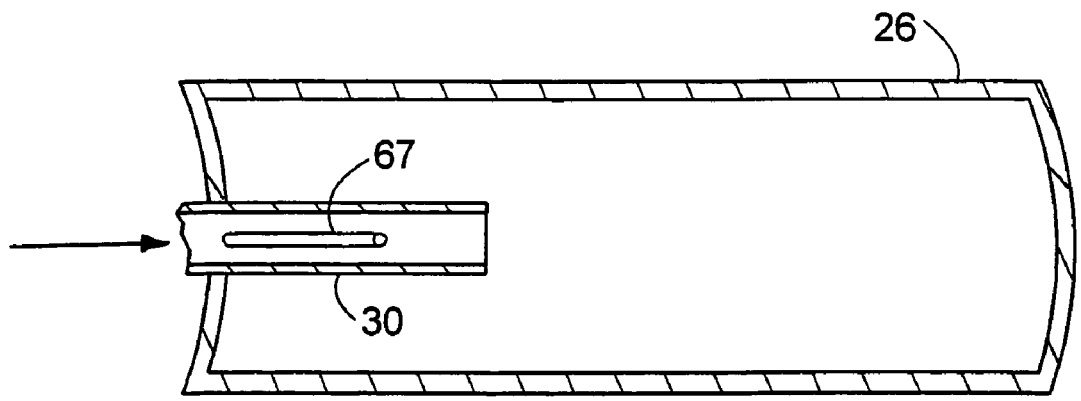
FIGS. 8A, 8B, and 8C illustrate an embodiment of a method of delivering an embolic composition.
Figure 8B:
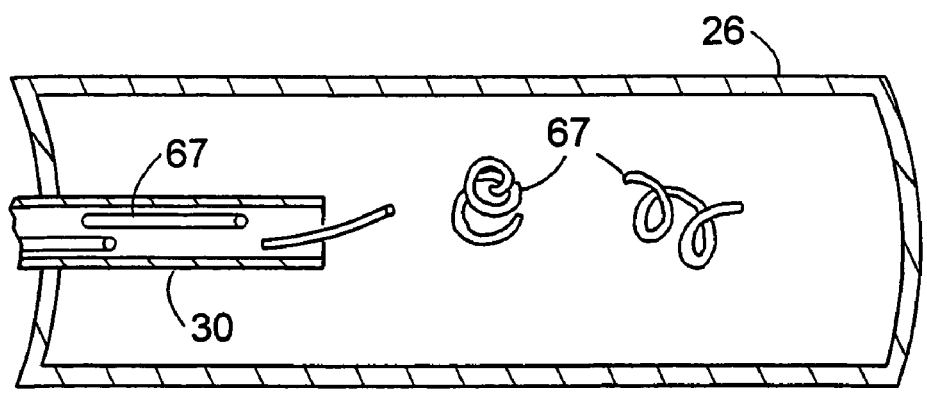
Figure 8C:
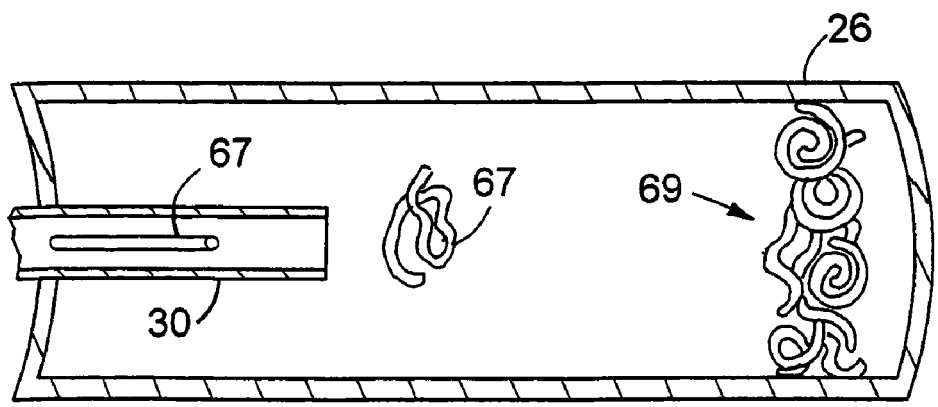

In other embodiments, the elongated particles can be formed to transition to a less elongated shape. Referring to FIGS. 8A, 8B, and 8C, particles 67 can be delivered through catheter 30 in a first, generally elongated form, such as a cylindrical or fiber-like form. After particles 67 are released, the particles are exposed to a stimulus that causes the particles to change shape. For example, particles 67 can change to spring-like coils, three-dimensional masses (such as balls), kinks, and/or zigzag members. The transitioned particles 67 can become entangled with each other to provide an effective occlusion 69. Particles 67 can have any of the features described herein (e.g., ridges, projections, and/or slots), in any combination. Particles 67 can be used with any of the particles described herein.

Figure 9B:
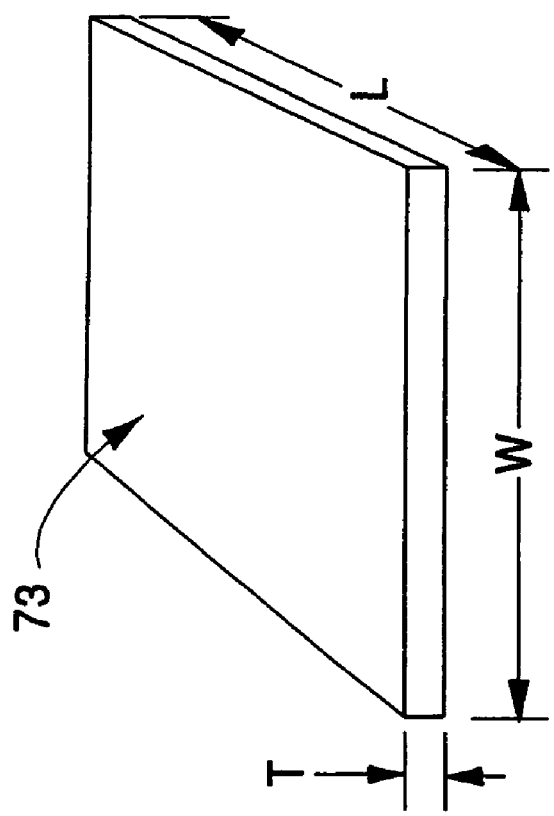
FIG. 9B is an illustration of an embodiment of a sheet-like embolic particle.
Figure 9A:
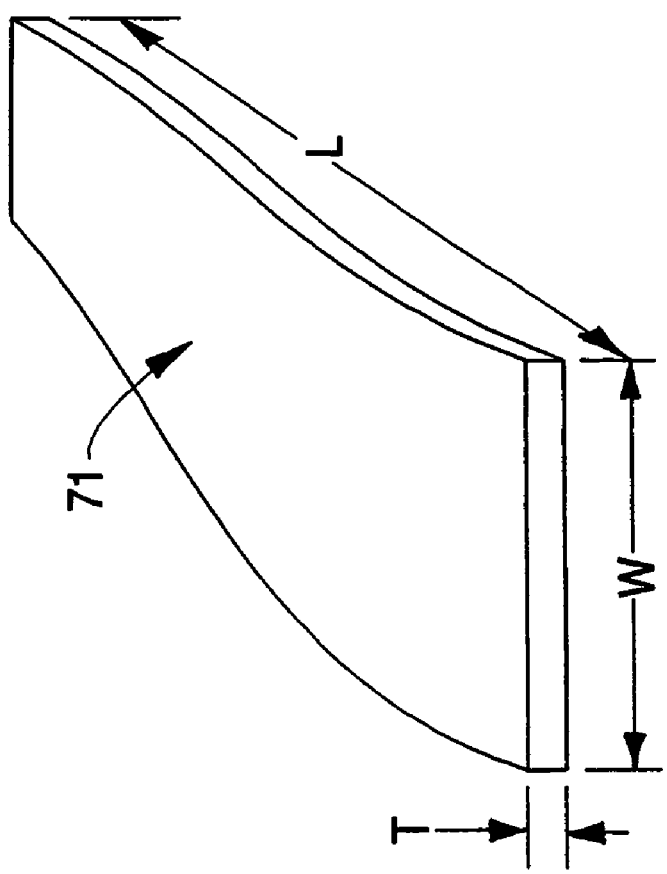
FIG. 9A is an illustration of an embodiments of a ribbon-like embolic particle.
Figure 12A:
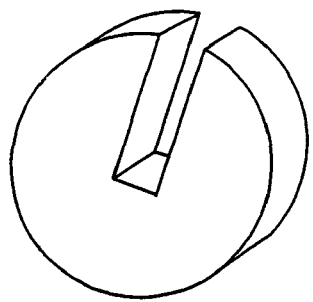
FIG. 12A is an illustration of an embodiment of an embolic particle having a slot.
Figure 12B:
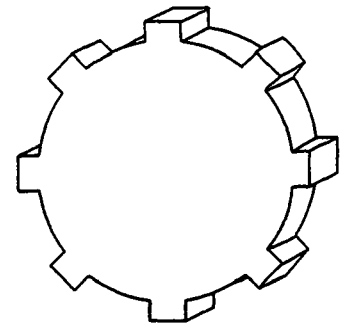
FIG. 12B is an illustration of an embodiment of a gear-shaped embolic particle.
Figure 12C:
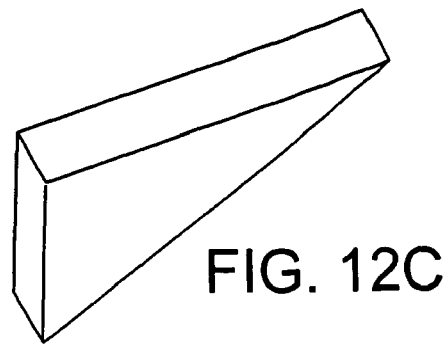
FIG. 12C is an illustration of an embodiment of a wedge-shaped embolic particle.

The particles are also not limited to the relatively three-dimensional structures shown in FIGS. 3A and 4-7. In some embodiments, the embolic particles can be relatively two-dimensional. That is, the embolic particles can have a very small thickness. Referring to FIGS. 9A and 9B, in some cases, the particles are ribbon-like (particle 71) or sheet-like (particle 73). The flat morphology of the particles allows them to be initially compacted (e.g., folded) to facilitate delivery, and subsequently expanded (e.g., unfolded) upon exposure to a stimulus. In some embodiments, particles 71 or 73 have a thickness (T) less than about 50 microns (e.g., less than about 40, 30, or 20 microns). Alternatively or in addition, particles 71 or 73 have a thickness (T) to width (W) ratio of between about 1.25:1 and about 10:1. For example, the aspect ratio can be greater than or equal to about 1.25:1, 2:1, 3:1, 4:1,5:1, 6:1, 7:1, 8:1, or 9:1; and/or less than or equal to about 10:1, 9:1, 8:1, 7:1, 6:1, 5:1, 4:1, 3:1, or 2:1. The length (L) of particles 71 and 73 can be as described above.

The shape memory material can be used to form embolic particles other than those described above. For example, the shape memory material can also be used to form embolic particles that are not substantially elongated. The shape memory material can be used to form generally spherical (e.g., completely spherical or egg-shaped) embolic particles (e.g., particles 56 and 58 shown in FIGS. 14 and 15A-15F, described below). For delivery, the generally spherical particles can be compacted to a generally oblate shape. Subsequently, the particles can be exposed to a stimulus that enlarges the particles, e.g., to the egg-shaped or spherical particles. Suitable dimensions for spherical embolic particles range from 1,500 microns to 2,000 microns in diameter, and are described in U.S. Ser. No. 09/519,263, filed Mar. 6, 2000, now abandoned, hereby incorporated by reference.

In other embodiments, the shape memory material can be used to form particles whose final form is oblate, e.g., like a red blood cell. Referring to FIGS. 10A-10B, an oblate particle 52 has a generally round or oval cross section and a relatively flat profile. The surface of particle 52 is generally curvilinear. At its central portion 53, the particle is depressed, such that the central portion is narrowed, and the perimeter 55 of the particle is thicker than the central portion. As a result, particle 52 is concave at central portion 53, and convex at its perimeter 55. The oblate shape allows particle 52 to easily flex (FIG. 10C) so that the particle can be easily delivered, e.g., flow through a catheter without aggregating. In some embodiments, particle 52 can have a width (W) of about 50 to about 1200 microns (e.g., greater than or equal to about 50, 200, 400, 600, 800, or 1000 microns; and/or less than or equal to about 1200, 1000, 800, 600, 400, or 200 microns), a maximum thickness ($T_{max}$) of about 1000 to about 1200 microns (e.g., greater than or equal to about 1000 or 1100 microns; and/or less than or equal to about 1200 or 1100), and a minimum thickness ($T_{min}$) of about 100 to about 200 microns (e.g., greater than or equal to about 100 or 150 microns; and/or less than or equal to about 200 or 150 microns). In other embodiments, central portion 53 is not depressed, e.g., the thickness of the oblate particle is generally constant.

Still other relatively non-elongated forms are possible. FIGS. 11A and 11B show a non-elongated embolic particle 54 having the generally star-shaped cross-section of particle 44, but without the extended length. The relatively short length can be less than about 100 microns (e.g., less than about 90, 80, 70, 60, 50, 40, 30, 20, or 10 microns). The cross-sectional shape of particle 54 can be modified similarly to the cross-sectional shape of particle 44. Similarly, particles 32, 40, and 48 (FIGS. 3A, 5, and 7) can be formed having the same cross-sections but without the extend lengths. FIGS.

12A, 12B, and 11C respectively show truncated embodiments of particle 32, particle 40, and particle 48 (without a slot).

Figure 13A:
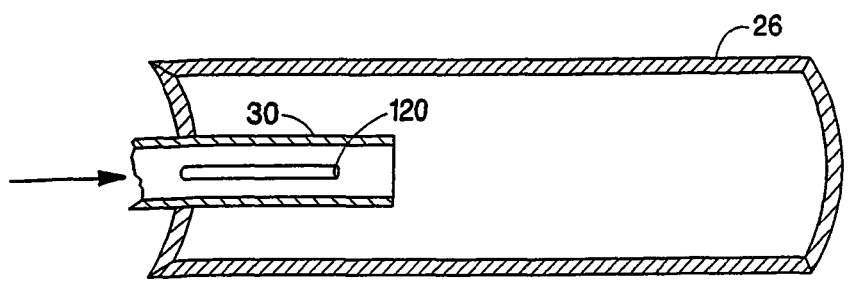
FIGS. 13A, 13B, and 13C illustrate an embodiment of a method of delivering an embolic composition.
Figure 13B:
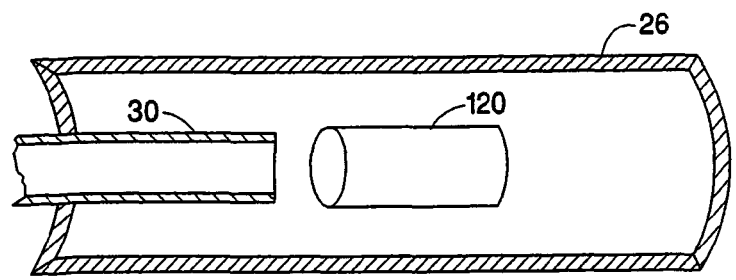
Figure 13C:
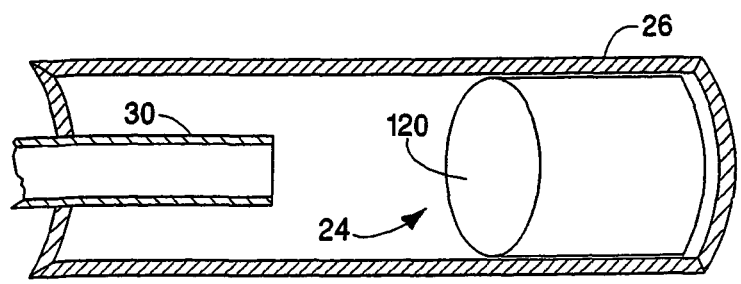

While the particles described herein can compose an embolic composition having a plurality of particles, in certain embodiments, the embolic composition includes only one particle. Referring to FIGS. 13A-13C, an embolic particle 120 (as shown, an elongated cylindrical particle) can be delivered to target site 24 in vessel 26 using catheter 30. During delivery, particle 120 is in a first state (e.g., a compacted state) as it passes through catheter 30. After particle 120 is released from catheter 30, the particle is transformed to a second state (e.g., an expanded state), and in the second state, the particle travels through vessel 26 and occludes the vessel. In some embodiments, smaller particles (e.g., as described herein) can be introduced before and/or after particle 120 is delivered to provide additional occlusion. Specific dimensions of particle 120 can be a function of the vessel in which the particle is to be used. In some embodiments, particle 120 has a final, average cross sectional diameter of about one millimeter to about forty-six millimeters. The length of particle 120 can be about one micron to about 50 mm, e.g., between about 3 and about 25 mm. Particle 120 can be formed into any of the shapes described herein using the material(s) described herein.

In some embodiments, the particles (e.g., the particles shown in FIGS. 3A and 4-12C) can be formed entirely of a material that does not exhibit shape memory characteristics ("a non-shape memory material"). The performance of the particles can be enhanced by the particular set shape or shapes described above. An example of a suitable non-shape memory material is a biocompatible polymer, such as polyvinyl alcohol (PVA) described in U.S. Ser. No. 10/215,594, filed Aug. 9, 2002, now pending hereby incorporated by reference. Other suitable materials include biocompatible ceramics, such as silica particles, described in U.S. Pat. No. 4,640,807 and EPO 067459, hereby incorporated by reference.

Another type of non-shape memory material is an absorbable polymer or a superabsorbable polymer. These polymers are porous materials that can absorb another material, such as a body fluid or a biocompatible agent, and expand from an initial (e.g., compacted) shape to a second (e.g., expanded) shape. Examples of polymers include hyaluronic acid (Medtronic Xomed™, Inc., MN) and hydrogels.

Mixtures of non-shaped memory materials can be used to make the particles. For example, a particle can include a core made of a polymer, such as PVA, and an outer surface made of a ceramic, such as silica. The porous outer surface can be used to store materials, such as a radiopaque material or an MRI-visible material, and/or to release a material, such as a therapeutic agent. In other embodiments, the core includes a ceramic and a polymer surrounds the core. The polymer can respond (e.g., change shape) during use as described above.

Figure 14:
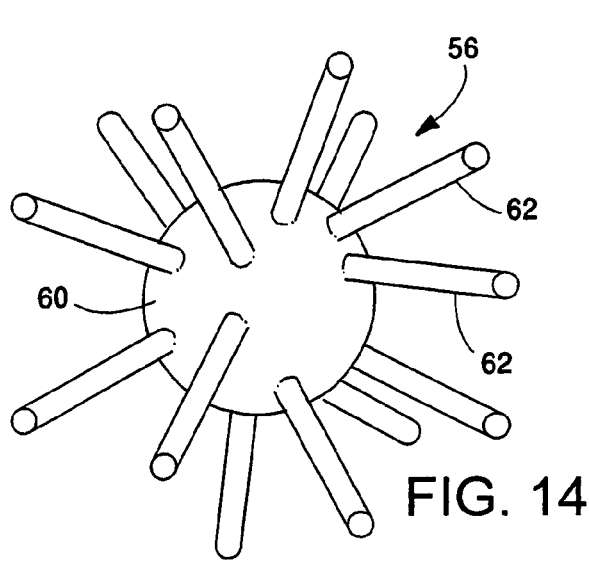
FIG. 14 is an illustration of an embodiment of an embolic particle having fibers.

In other embodiments, the embolic particles can be formed of a combination of a shape memory material and a non-shape memory material. For example, referring to FIG. 14, particle 56 can include a generally spherical body 60 made of a non-shape memory material, and a plurality of fibers or filaments 62 made of a shape memory material extending from the surface of the body. In some cases, fibers 62 are formed such that the fibers have a free end exposed (as shown in FIG. 14); in other cases, the ends of the fibers are embedded in body 60 such that the fibers form a loop extending from the body. Since fibers 62 are made of a shape memory material, particle 56 can be compacted by folding the fibers to body 60 during delivery of the embolic composition, thereby enhancing delivery. Subsequently, fibers 62 can be unfolded in the body so that particles 56 can interact (e.g., tangle) with other and aggregate. In other embodiments, body 60 includes a shape memory material and fibers 62 include a non-shape memory material. The non-shape memory material can be as described above and can further include synthetic materials, such as polyester, nylon, DACRON®, PTFE, polypropylene, Kevlar®, natural materials, such as silk, collagen, or hair; alginate; or suture-based materials. Particle 56 can be formed wholly of a shape memory material or a non-shape memory material.

Figure 15A:
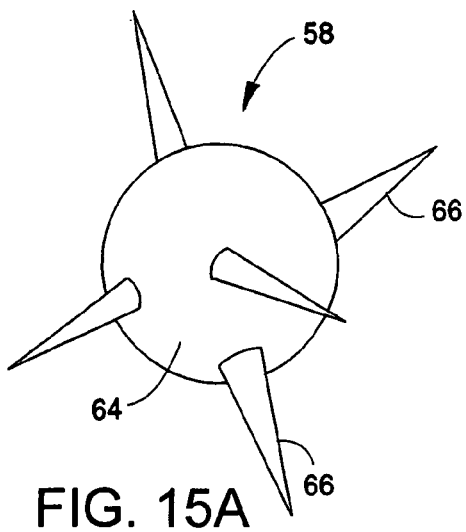
FIGS. 15A, 15B, 15C, 15D, 15E, and 15F are illustrations of embodiments of embolic particles having various projections.
Figure 15B:
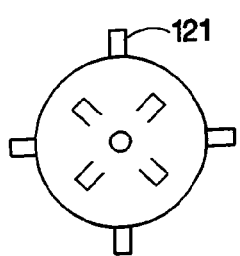
Figure 15C:
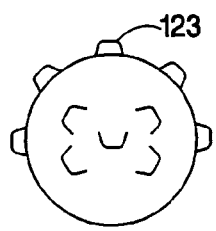
Figure 15D:
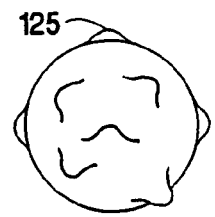
Figure 15E:
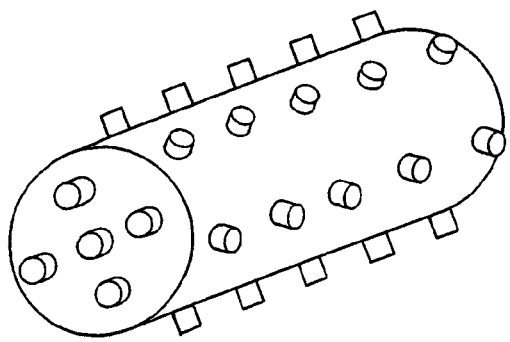
Figure 15F:
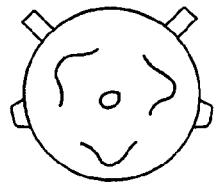

As another example, referring to FIG. 15A, particle 58 includes a generally spherical body 64 and a plurality of spikes 66 (not drawn to scale) extending from the body. Body 64 can be formed of a non-shape memory material, and spikes 66 can be formed of a shape memory material. Like fibers 62, during use, spikes 66 can be folded and subsequently unfolded. Spikes 66 can have a length of about 100 microns. In other embodiments, body 64 is formed of a shape memory material, and spikes 66 are formed of a non-shape memory material. Particle 58 can be formed wholly of a shape memory material or a non-shape memory material. In other embodiments, projections other than spikes 66 can be used. For example, the projections can include rods 121 (FIG. 15B), frustoconical projections 123 (FIG. 15C), or bumps 125 (FIG. 15D). The projections can be evenly or unevenly distributed about a particle. The projections can be formed, wholly or in selected portions, of any of the embodiments of particles described herein, such as particles 32, 36, 40, 44, 48, or 120 (FIG. 15E). Different types of projections (e.g., rods and bumps), in any combination, can be formed on a particle (e.g., FIG. 15F).

In some embodiments, the embolic particles described herein can be surface modified, for example, by forming a coating on the particles. For example, the particles can include a coating of a lubricious material, such as Glidex®, Mediglide® (silicone-based coatings), or Hydropass™ (water-based coatings), that enhance delivery of the particles (e.g., by preventing premature aggregation). The particles can include a coating of a material that changes upon exposure to a predetermined condition. For example, the coating material can include a hydrogel, alginate, or a starch that swells upon contact with a liquid, a change in temperature, and/or a change in pH. The soft, swollen coating can help the particles to easily deform and provide tight packing. The coating material can be soluble material, such as one that can dissolve in bodily fluids (described below) or another fluid subsequently delivered through the catheter. The soluble material can retard the transition of the shape memory material, for example, by acting as a thermal barrier. In embodiments in which the embolic particles include an absorbable material, the soluble material can delay absorption. An absorbable or bio-absorbable material is capable of dissolving upon exposure to bodily fluid at a known rate. Polymer coating materials which can be used as a bio-absorbable coating include gelatin; polylactic acid (e.g., poly-L-lactic acid, blends of DL-lactic acid, or poly(lactic acid-co-glycolic acid); polyglycolic acid; polysaccharides such as celluloses (e.g., hydroxymethylpropylcellulose), starches, dextrans, alginates and derivatives; and chlorohexidine gluconate, among others. The bio-absorbable coating thickness can be varied to regulate the amount of absorption, the type of bio-absorbable coating thickness can be varied to regulate the amount of absorption, and the type of bio-absorbable coating can be selected to absorb certain predetermined fluids, such as blood. The bio-absorbable material can also act as a matrix that encourages cell growth into an embolized vessel.

Other materials can be used. Suitable materials include, for example, polycarboxylic acids, cellulosic polymers, including cellulose acetate and cellulose nitrate, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polycaprolactone, polyhydroxybutyrate, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage, and derivatives thereof, an extracellular matrix component, hyaluronic acid, chitosan, or another biologic agent or a suitable mixture of any of these. Other examples include polyacrylic acid, available as HYDROPLUS® (Boston Scientific Corporation, Natick, Mass.), and described in U.S. Pat. No. 5,091,205; polyisocyanates (e.g., such that the particles can become instantly lubricious when exposed to body fluids, see, for example, U.S. Pat. No. 5,091,205); polycaprolactone (e.g., a copolymer of polylactic acid and polycaprolactone, or copolymer of polycaprolactone and butylacrylate); tyrosine-derived polycarbonates and arylates; polyphosphazenes; polyiminocarbonates; polydimethyltrimethylcarbonates; biodegradable calcium phosphates (e.g., zinc calcium phosphates); cyanoacrylates; polydioxanone; polypropylene fumarate; polydepsipeptides; maleic anhydride copolymers; and anhydrous polyanhydrides.

In some embodiments, the particles can include, applied to the surface of the particles, one or more therapeutic agents. The therapeutic agents can be released upon contact with bodily fluids. The soluble material described above can be used to control the release of the therapeutic agents. The agents can be negatively charged, cationically charged, amphoteric, or neutral. The therapeutic agents can be formed in the bulk of the particles or applied to the surfaces of the particles.

Some examples of therapeutic agents are described in U.S. Ser. No. 10/232,265, filed Aug. 30, 2002, now pending hereby incorporated by reference. Examples of other therapeutic agents include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; anti-cancer or antineoplastic/antiproliferative/anti-miotic agents such as paclitaxel, 5-fluorouracil, cisplatin, vinblastine, vincristine, cladribine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Alternatively or in addition, the surface of the particles can be textured, e.g., roughened. The textured surface can increase the surface area of the particles, thereby allowing more materials, such as a therapeutic agent, to be applied to the surface. The textured surface can provide pits or craters in which coating materials can be placed. Techniques for creating a textured surface include micrograzing, cryogenic pulverization, and/or microcracking.

Alternatively or in addition to the surface modification, the internal structure of the embolic particles can be modified. For example, the embolic particles can surround (e.g., encapsulate) a mass including diagnostic agent(s) such as a radiopaque material, a material that is visible by magnetic resonance imaging (MRI), and/or an ultrasound contrast agent. The materials or agent allows the particles to be tracked and monitored, e.g., by X-ray fluoroscopy, MRI, or ultrasound imaging. The radiopaque material (e.g., powder), MRI-visible material, and/or ultrasound visible material can be mixed with the material of the embolic particles, e.g., shape memory polymer, and formed into the particles. In some cases, the radiopaque material, MRI-visible material, and/or ultrasound visible material can be applied to the surface of the particles, for example, by compounding with one or more of the coating materials described above. Alternatively or in addition, the radiopaque material can be a mass placed in the particles. Examples of radiopaque materials include high-density metals, such as tantalum, tungsten, platinum, palladium, or gold.

Examples of MRI visible materials include non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni). Powder of MRI visible materials can be mixed with the material of the embolic particles, e.g., shape memory polymer.

The ultrasound contrast agent can be any material that enhances visibility during ultrasound imaging. An ultrasound contrast agent can include a suspension having trapped bubbles of sufficient size to deflect sound waves.

In other embodiments, referring to FIG. 16, an embolic particle 70 can be formed to define a cavity 72 in which a therapeutic agent can be placed and sealed. Cavity 72 can be sealed with a material that degrades or dissolves upon exposure to a predetermined condition, such as contact with bodily fluids, a change in pH, or a change in energy (e.g., temperature). When the sealant degrades or dissolves, the therapeutic agent can be released in the body. Suitable materials for sealing cavity 72 include polyvinyl pyrrolidone (PVP) (which dissolves in a solution having a selected pH, e.g., about >7.4), polyvinyl acetates, vinyl or collagen based glues or gelatins, and other degradable materials described in Buscemi et al., U.S. Pat. No. 5,443,495, hereby incorporated by reference.

In use, the embolic particles can be delivered to an intended site by, for example, passing the particles through a catheter emplaced near the intended site. In embodiments in which the particles include a shape memory material, the particles are typically carried by a biocompatible solution having a temperature less than the transition temperature to inhibit the shape memory material from transitioning.

Mixtures or combinations of different embolic particles can be introduced (simultaneously or sequentially) during an embolization procedure so that the particles can interact synergistically. Differently shaped particles can be used together. For example, referring to FIG. 17A, three-dimensional particles 41, such as spheres and/or cylinders, can be introduced (before, after, or simultaneously) with two-dimensional particles 43, such as elongated, ribbon-like particles or flat particles. When the particles interact and aggregate, the ribbons or flat particles can fill the voids between the spheres, thereby providing a more effective occlusion. As another example, referring to FIG. 17B, ribbon-like particles 43 can be delivered with particles 45 having slots. The ribbon-like particles can interact (e.g., engage with or interlock with) the slots, thereby self-assembling to a more solid structure.

Alternatively or in addition, particles of different sizes can be used together (e.g., sequentially or simultaneously). Referring to FIG. 18, relatively large particles 47 can be used to provide the general structure of an occlusion, while the smaller particles 49 can occupy the spaces between the large particles. The large and small particles can be delivered simultaneously or sequentially. For example, relatively large particles can be delivered first to form the general structure an occlusion, and relative small particles can subsequently be delivered to fill any spaces between the large particles.

Figure 20:
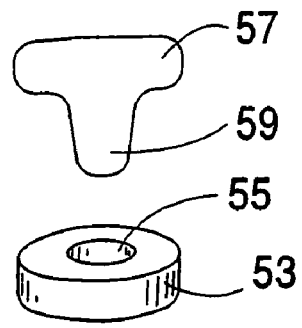
FIG. 20 is an illustration of two embolic particles having complementary features.
Figure 21A:
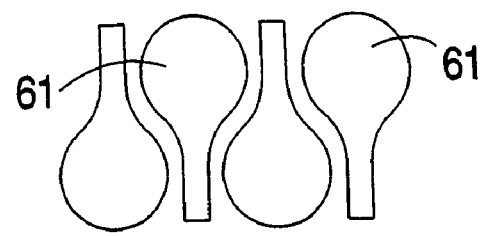
FIGS. 21A and 21B are illustrations of embodiments of embolic particles having teardrop shapes.
Figure 21B:
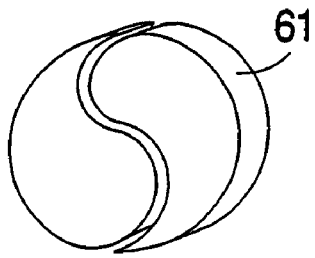
Figure 22A:
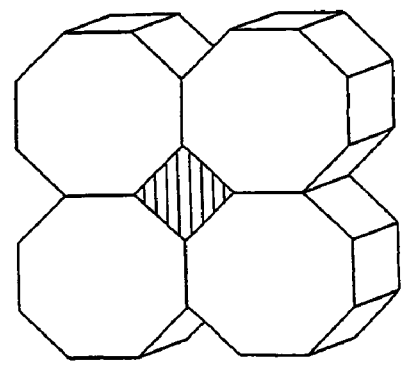
FIGS. 22A, 22B, and 22C are illustrations of embodiments of occlusions.
Figure 22B:
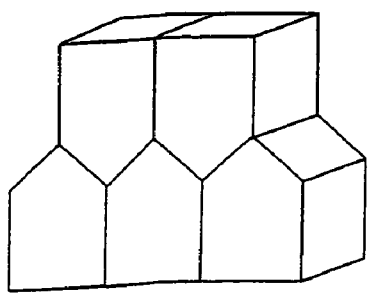
Figure 22C:
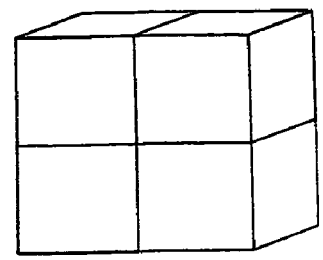

Other combinations including particles with complementary (e.g., interlocking) shapes are possible. For example, referring to FIG. 19, spherical particles 41 can be delivered with particles 51 having concave portions (e.g., oblate particles 52 described below) that receive portions of the spherical particles. Particles 51 are capable of filling voids between spherical particles 41. Other complementary particles capable of interlocking include particles 53 with openings 55, and particles 57 having a portion 59 (e.g., a projection) capable of penetrating the opening (FIG. 20). Other complementary particles 61 include those with teardrop shapes (FIGS. 21A and 21B) having a relatively small portion that extends curvilinearly to a relatively large portion. The particles can form relatively flat, two-dimensional structures, or three-dimensional structures (e.g., two particles can engage to form a sphere). In other embodiments, complementary particles have one or more surfaces that are relatively flat, i.e., planar. For example, the particles can be cubic or icosahedral particles. Referring to FIGS. 22A, 22B, and 22C, particles having flat surfaces can form occlusions by stacking like blocks in which the flat surfaces contact each other. The particles can be of similar or same size (e.g., FIGS. 22B and 22C) or different size (e.g., FIG. 22A).

Particles having different physical and/or chemical properties can be used together. For example, particles having different hardness (e.g., durometer) can be used together. Particles having different surface properties can be delivered together. For example, hydrophobic particles can be surface modified with a dissolvable hydrophilic coating, and introduced together with unmodified hydrophobic particles. Since the modified and unmodified particles have different hydrophobicity/hydrophilicity, the particles tend not to aggregate. When the hydrophilic coating dissolves in the body to expose the hydrophobic surface, the particles can aggregate to form an occlusion.

The embolic particles can be delivered with agents in different physical states. For example, the embolic particles can be delivered using a contrast agent (such as such as Omnipaque™ Renocal®) or a radiopaque agent so that the delivery of the particles can be tracked. In embodiments in which the particles can absorb liquids, absorption of the contrast agent allows the particles to be monitored, e.g., after occlusion. The embolic particles can be delivered with liquid embolic materials (such as n-butyl cyanoacrylates (NBCA)), foam embolic materials (such as Ivalon® (PVA foam)), and/or gel embolics materials (such as hydrogels). NBCA is capable of polymerizing when contacted with an ionic substance, such as blood, saline ionic contrast media, and vessel epithelium. Polymerization time can be altered (e.g., prolonged) by adding varying amounts of glacial acetic acid and/or oil-based contrast agents, e.g., ethiodol or pantopaque. Other compositions capable of being introduced into the body as a liquid from which a solid thereafter precipitates are described in U.S. Pat. No. 6,575,896 and exemplified by Enteryx® (available from Boston Scientific Corp., Natick, Mass.). An example of a composition includes a biocompatible solvent (e.g., DMSO), a biocompatible polymer (e.g., cellulose acetate), and a contrast agent (e.g., barium sulfate). Other materials capable of solidifying in vivo include those used in polymer endoluminal paving and sealing (PEPS), described, for example, in U.S. Pat. No. 6,443,941. Still other examples include inorganic gels and other materials described in U.S. Pat. No. 6,296,632.

The embolic particles can be used with hemostatic agents. Agents include Gelfoam® (a gelatin sponge available from Upjohn Co., Kalamazoo, Mich.) and Avitene® (a microfibrillar collagen (e.g., 40-60 micron particles) available from Avicon Inc., Fort Worth, Tex.). Other examples include fibrin, fibrin glue, blood clotting precursors, other collagen-based agents(e.g., Collastat™, Superstat™, and Instat™), cellulose (e.g., Oxycel™ and Surgicel™), calcium alginate, hyaluronic acid, platelets, thrombin, and cryoprecipitate. In some cases, clotting can be promoted by charging the embolic particles, e.g., their surfaces. Other examples include silk sutures and microcoils (which can be used to build a framework or a mesh on which the particles can accumulate and occlude); fibered stainless steel (e.g., from Gianturco); platinum microcoils with or without Dacron® fibers (available from E.I. du Pont de Nemours and Co., and Target Therapeutics Boston Scientific); Guglielmi detachable coils (long, non-fibered platinum microcoils (available from Target Therapeutics Boston Scientific); and interlocking detachable coils. Alternatively or in addition, embolic therapy can include adding a vasospastic agent (such as serotonin and oxyhemoglobin) to constrict a blood vessel locally and to cause local occlusion and/or thrombus.

Mixtures of embolic particles can be delivered simultaneously or in a predetermined sequence. For example, relatively large particles can be delivered first to form the general structure an occlusion, and relative small particles can subsequently be delivered to fill any spaces between the large particles. Similarly, three-dimensional particles can be delivered first, followed by two-dimensional particles.

Figure 23A:
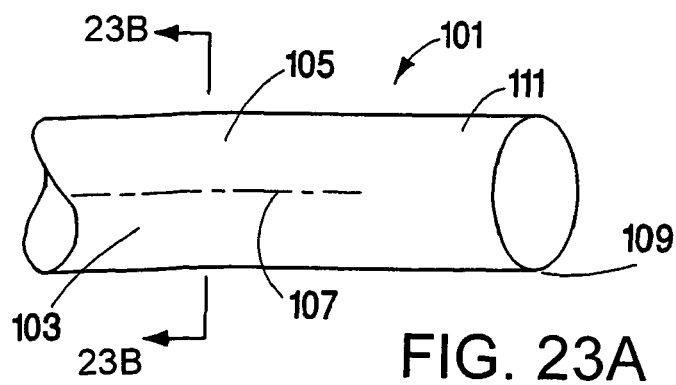
FIG. 23A is an illustration of an embodiment of a catheter.
Figure 23B:
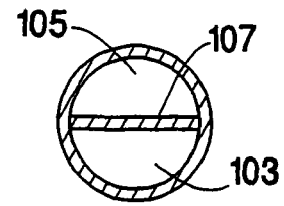
FIG. 23B is a cross-sectional view of the catheter of FIG. 23A, taken along line 23B-23B.
Figure 24A:
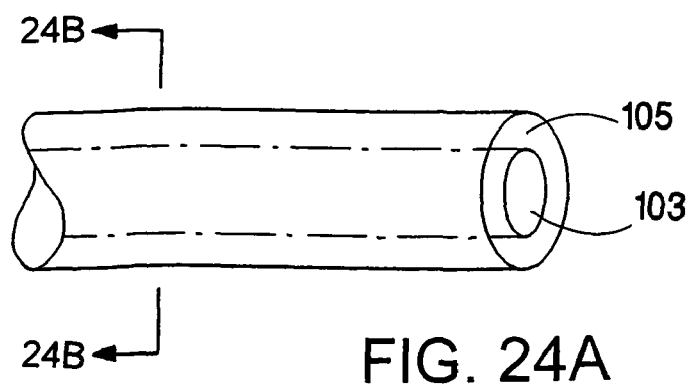
FIG. 24A is an illustration of an embodiment of a catheter.
Figure 24B:
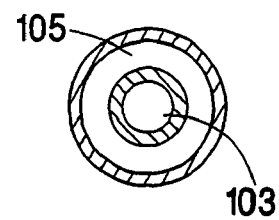
FIG. 24B is a cross-sectional view of the catheter of FIG. 24A, taken along line 24B-24B.

Mixtures of embolic particles can be delivered using a multi-lumen catheter and/or syringe. For example, referring to FIGS. 23A and 23B, a catheter 101 includes two lumens 103 and 105 separated by a wall 107. Wall 107 terminates proximally of the distal tip 109 of catheter 101, so at the distal tip, the catheter has a mixing chamber 111. During use, one type of embolic particles can be delivered through lumen 103, and another type of embolic particles can be delivered through lumen 105. Lumens 103 and 105 keep the particles separated so that, for example, they do not prematurely interact (e.g., aggregate or clog) inside catheter 101. The particles can then mix in chamber 111 before they are introduced into the body. In other embodiments, wall 107 terminates at distal tip 109, i.e., the catheter does not include a mixing chamber. Lumens 103 and 105 can be formed coaxially (FIGS. 24A and 24B), vis-à-vis, side-by-side, with or without a mixing chamber. The multi-lumen catheter or syringe can include more than two lumens, depending, for example, on the number of types of embolic particles to be delivered.

The embolic particles can be used to embolize vascular malformations and tumors, for example as a preoperative procedure to reduce surgical morbidity and/or mortality related to excessive interoperative blood loss. In these cases, occlusion of body vessels is typically temporary. In other cases, embolization is used as a definitive treatment, such as when the patient is not considered a good surgical candidate (e.g., because of poor heath, previously unsuccessful surgical attempts, inaccessible surgical site, traumatic hemorrhagic conditions, and/or high surgical risk). In these cases, occlusion of vessels is typically permanent. For example, embolization of internal mammary arteries and lumbar arteries can be used in endovascular abdominal aortic aneurysm repairs to treat Type 2 endoleaks.

Furthermore, in other embodiments, the embolic compositions can be used as pharmaceutically acceptable compositions in the treatment of, for example, fibroids, tumors, internal bleeding, AVMs, hypervascular tumors, fillers for aneurysm sacs, endoleak sealants, arterial sealants, puncture sealants and occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

The magnitude of a therapeutic dose of the embolic composition can vary based on the nature, location and severity of the condition to be treated and the route of administration. A physician treating the condition, disease or disorder can determine effective amount of embolic composition. An effective amount of embolic composition refers to the amount sufficient to result in amelioration of symptoms or a prolongation of survival of the patient. The embolic compositions can be administered as pharmaceutically acceptable compositions to a patient in any therapeutically acceptable dosage, including those administered to a patient intravenously, subcutaneously, percutaneously, intratrachealy, intramuscularly, intramucosaly, intracutaneously, intra-articularly, orally or parenterally.

Compositions containing the embolic particles can be prepared in calibrated concentrations of the embolic particles for ease of delivery by the physician. The density of the composition can be from about 1.1 to 1.4 g/cm$^3$, or from about 1.2 to about 1.3 g/cm$^3$ in saline solution. Suspensions of the embolic particles in saline solution can be prepared to form stable suspensions over duration of time. The suspensions of embolic particles can be stable from 1 to 10 minutes, 2-7 minutes or 3 to 6 minutes. The physician can determine concentration of embolic particles by adjusting the weight ratio of the embolic particles to physiological solution.

If weight ratio of the embolic particles is too small, too much liquid could be injected in a blood vessel, possibly allowing the embolic particles to stray into lateral vessels. In embodiments, the weight ratio of the embolic particles to the physiological solution is about 0.01 to 15% by weight.

In other embodiments, the embolic particles can be used for lung volume reduction, such as to treat any of the Chronic Obstructive Pulmonary Diseases (COPD). For example, a portion of the lung may be collapsed by obstructing an air passageway communicating with the portion of the lung to be collapsed. The air passageway may be obstructed by placing the embolic particles in the air passageway. The particles prevent air from being inhaled into or exhaled from the lung portion. Once the air passageway is sealed, the residual air within the lung can be absorbed over time to cause the lung portion to collapse. In other embodiments, the lung portion can be collapsed by inserting a conduit into the air passageway communicating with the lung portion, pulling a vacuum in the lung portion through the conduit to collapse the lung portion, and maintaining the lung portion in a collapsed state by sealing the air passageway with the embolic particles. To efficiently pull the vacuum in the lung portion to be collapsed, the space between the outer surface of the conduit and the inner surface of the air passageway may be sealed as the vacuum is pulled. The air passageway can be sealed while the lung portion is collapsed.

In some embodiments, the embolic particles described above can be used for tissue bulking. For example, the particles can be used to treat intrinsic sphincteric deficiency (ISD), vesicoureteral reflux, gastroesophageal reflux disease (GERD), and vocal cord paralysis, e.g., to restore glottic competence in cases of paralytic dysphonia. The particles can be used as a graft material or a filler to fill and/or to smooth out soft tissue defects, such as for reconstructive or cosmetic applications, e.g., surgery. Examples of applications include reconstruction of cleft lips; scars, e.g., depressed scars from chicken pox or acne scars; indentations resulting from liposuction; wrinkles, e.g., glabella frown wrinkles; and soft tissue augmentation of thin lips. Other applications are described in U.S. Ser. No. 10/231,664, filed Aug. 30, 2002, now pending hereby incorporated by reference.

All publications, applications, references, and patents referred to in this application are herein incorporated by reference in their entirety.

Other embodiments are within the claims.

What is claimed is:

1. A composition, comprising:
   a first plurality of embolic particles, each of the first plurality of embolic particles comprising a shape memory material; and
   saline,
   wherein:
   the embolic particles are in the saline;
   each of the first plurality embolic particles is generally spherical; and
   the shape memory material comprises an alloy.

2. The composition of claim 1, wherein the alloy is a material selected from the group consisting of a nickel-titanium alloy.

3. The composition of claim 1, wherein each of the first plurality the particles is non-bioabsorbable in a body.

4. The composition of claim 1, wherein each of the first plurality the particles further comprises a therapeutic agent.

5. The composition of claim 4, wherein each of the first plurality the particles defines a cavity, and the therapeutic agent is in the cavity.

6. The composition of claim 1, wherein each of the first plurality the particles comprises a radiopaque material.

7. The composition of claim 6, wherein the radiopaque material is selected from the group consisting of gold, tantalum, platinum, and tungsten.

8. The composition of claim 1, wherein each of the first plurality the particles has a groove.

9. The composition of claim 1, wherein each of the first plurality the particles comprises a portion capable of dissolving in a body.

10. The composition of claim 1, wherein each of the first plurality the particles further comprises a second material that does not include a shape memory material.

11. The composition of claim 10, wherein the second material is selected from the group consisting of polyester, nylon, polytetrafluoroethylene, polypropylene, poly-paraphenylene terephthalamide, silk, collagen, hair, and alginate.

12. The composition of claim 1, further comprising a second plurality of embolic particles, a particle in the second plurality having a different shape than a particle in the first plurality of embolic particles.

13. The composition of claim 1, further comprising a second plurality of embolic particles, a particle in the second plurality having a different size than a particle in the first plurality of embolic particles.

14. The composition of claim 1, further comprising a second plurality of embolic particles, a particle in the second plurality having a different hardness than a particle in the first plurality of embolic particles.

15. The composition of claim 1, further comprising a second, non-solid embolic material.

16. The composition of claim 15, wherein the second embolic material is in the form of a liquid, a gel, or a foam.

17. The composition of claim 1, wherein each of the first plurality the particles comprises a material capable of increasing in volume upon exposure to a predetermined stimulus.

18. The composition of claim 17, wherein the material comprises a hydrogel.

19. The composition of claim 10, wherein the second material is selected from the group consisting of polyester, nylon, polytetrafluoroethylene, polypropylene, silk, collagen, hair, and alginate.

20. The composition of claim 11, wherein the second material comprises polyethylene terephthalate.

* * * * *

UNITED STATES PATENT AND TRADEMARK OFFICE
CERTIFICATE OF CORRECTION

| | | |
|---|---|---|
| PATENT NO. | : 7,901,770 B2 | |
| APPLICATION NO. | : 10/791103 | |
| DATED | : March 8, 2011 | |
| INVENTOR(S) | : Paul DiCarlo et al. | |

It is certified that error appears in the above-identified patent and that said Letters Patent is hereby corrected as shown below:

1.) Column 1, line 10, Paragraph 2: after "10/700,970" insert --,--.

Signed and Sealed this
Tenth Day of May, 2011

David J. Kappos
*Director of the United States Patent and Trademark Office*